US010723809B2

(12) United States Patent
Mitchell et al.

(10) Patent No.: US 10,723,809 B2
(45) Date of Patent: Jul. 28, 2020

(54) MICROCARRIERS, MATRICES AND SCAFFOLDS FOR CULTURING MAMMALIAN CELLS AND METHODS OF MANUFACTURE

(71) Applicants: HOWARD UNIVERSITY, Washington, DC (US); James W. Mitchell, Durham, NC (US); Dazhi Yang, Gaithersburg, MD (US)

(72) Inventors: James W. Mitchell, Durham, NC (US); Dazhi Yang, Gaithersburg, MD (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 15/560,141

(22) PCT Filed: Mar. 18, 2016

(86) PCT No.: PCT/US2016/023248
§ 371 (c)(1),
(2) Date: Sep. 20, 2017

(87) PCT Pub. No.: WO2016/154048
PCT Pub. Date: Sep. 29, 2016

(65) Prior Publication Data
US 2018/0094080 A1  Apr. 5, 2018

Related U.S. Application Data
(60) Provisional application No. 62/136,241, filed on Mar. 20, 2015.

(51) Int. Cl.
*C08B 15/02* (2006.01)
*C08B 15/06* (2006.01)
(Continued)

(52) U.S. Cl.
CPC ............ *C08B 15/005* (2013.01); *C08B 15/02* (2013.01); *C08B 15/06* (2013.01); *C08H 1/00* (2013.01); *C12N 5/0075* (2013.01)

(58) Field of Classification Search
None
See application file for complete search history.

(56) References Cited

U.S. PATENT DOCUMENTS

| 4,663,163 | A |   | 5/1987  | Hou et al. |
| 4,788,280 | A | * | 11/1988 | Billmers ............... C08B 11/04 162/158 |

(Continued)

FOREIGN PATENT DOCUMENTS

| WO |  01/07486 A1  | 2/2001 |
| WO | 2014/029888 A2 | 2/2014 |
| WO | 2016/154043 A1 | 9/2016 |

OTHER PUBLICATIONS

Polyallylannine grafted cellulose gel as high capacity anion exchanger, Kuga et al. Journal of Chromatography A, 946 (2002) 283-289 (Year: 2002).*

(Continued)

*Primary Examiner* — Peter A Salamon
(74) *Attorney, Agent, or Firm* — Sughrue Mion, PLLC

(57) ABSTRACT

Microcarriers, matrices and scaffolds for growing mammalian cells are provided which include copolymer particles and matrices comprising of polysaccharide-polyamine copolymers. The copolymeric particles and matrices have a pore size of at least 50 microns and permit the mammalian cells to grow both on an exterior surface of the particles and matrices and within an interior of the particles and matrices. Methods for making such microcarriers, matrices and scaffolds, and compositions are also provided. Methods for (Continued)

growing mammalian cells utilizing such microcarriers, matrices and scaffolds and compositions are also provided.

17 Claims, 14 Drawing Sheets

(51) Int. Cl.
  *C08B 15/00* (2006.01)
  *C08H 1/00* (2006.01)
  *C12N 5/00* (2006.01)

(56) References Cited

U.S. PATENT DOCUMENTS

| | | |
|---|---|---|
| 5,496,545 A | 3/1996 | Holmes-Farley et al. |
| 5,766,908 A | 6/1998 | Klein et al. |
| 7,001,891 B1 * | 2/2006 | Domb ................ C08B 37/0018 435/455 |
| 8,163,799 B2 | 4/2012 | Dhal et al. |
| 8,889,738 B2 | 11/2014 | Dhal et al. |
| 8,900,560 B2 | 12/2014 | Dhal et al. |
| 2004/0010137 A1 | 1/2004 | Jaschinski et al. |
| 2005/0002893 A1 | 1/2005 | Goldmann |
| 2008/0317861 A1 | 12/2008 | Guan |
| 2010/0272804 A1 | 10/2010 | Lu |
| 2012/0237470 A1 | 9/2012 | Dhal et al. |

OTHER PUBLICATIONS

European Patent Office, Extended European Search Report dated Nov. 13, 2018 for European Patent Application No. 16769444.7, 7 pages.

Patent Cooperation Treaty, International Search Report and Written Opinion of the International Searching Authority for International Application No. PCT/US2016/023248 dated May 31, 2016, 13 pages.

Kuga, Shigenori, and Kim, Ung-Jin, "Polyallylamine-grafted cellulose gel as high-capacity anion-exchanger," Journal of Chromatography A, 946, 2002, pp. 283-289.

Patent Cooperation Treaty, International Search Report and Written Opinion of the International Searching Authority for International Application No. PCT/US2016/023237 dated Jun. 10, 2016, 17 pages.

* cited by examiner

Microcrystalline Cellulose

Cationic Copolymers of Cellulose
(Stained with Eosin 20X)

Cationic Copolymers of Cellulose
(400X)

Mucin

Cationic Copolymers of Mucin
(Stained with Eosin 20X)

Cationic Copolymers of Mucin
(400X)

FIG. 4A          FIG. 4B          FIG. 4C
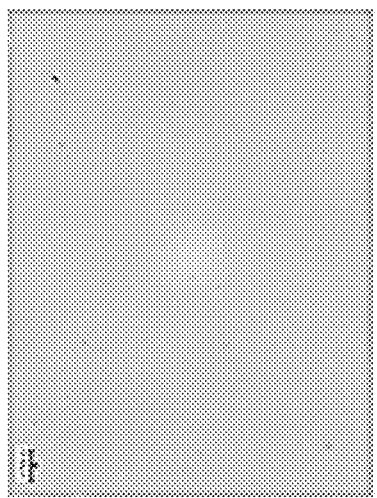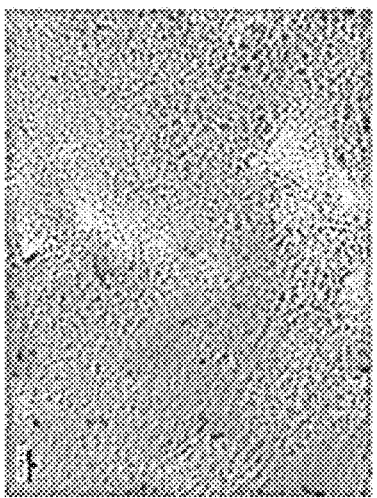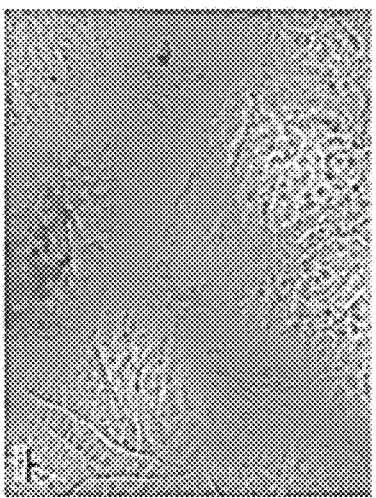
FIG. 4D          FIG. 4E          FIG. 4F
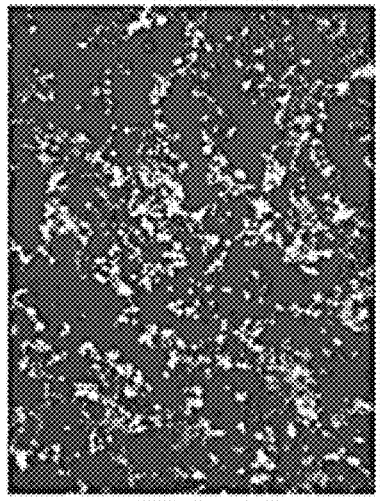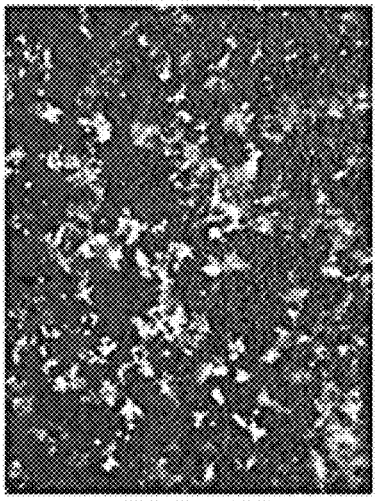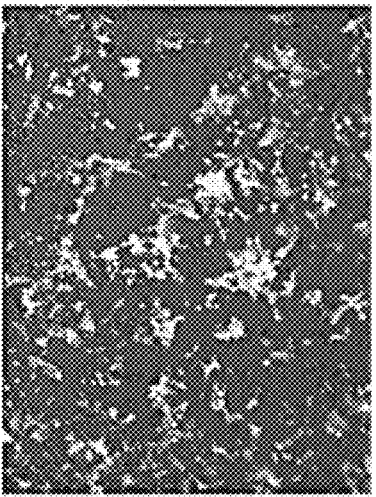
FIG. 4G          FIG. 4H          FIG. 4I
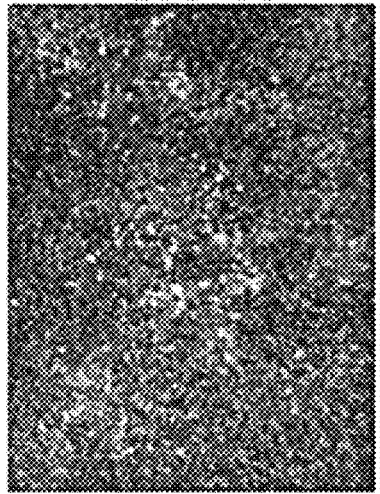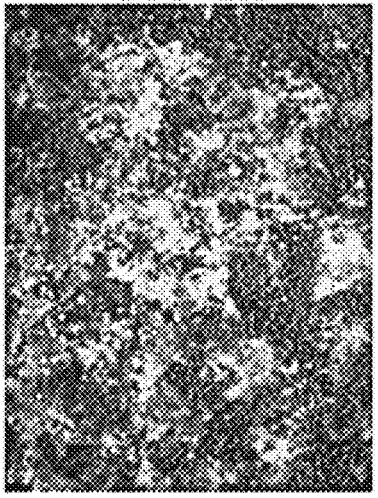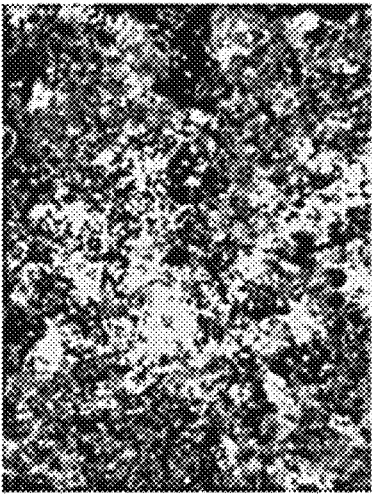
Poly L-lysine      Cationic Copolymers      Cationic Copolymers
                   of Cellulose              of Mucin

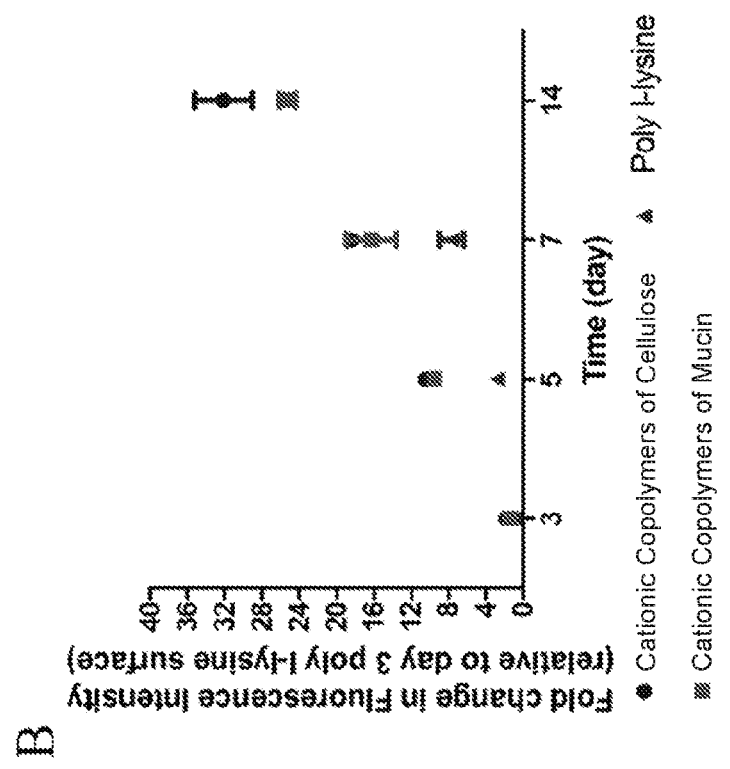
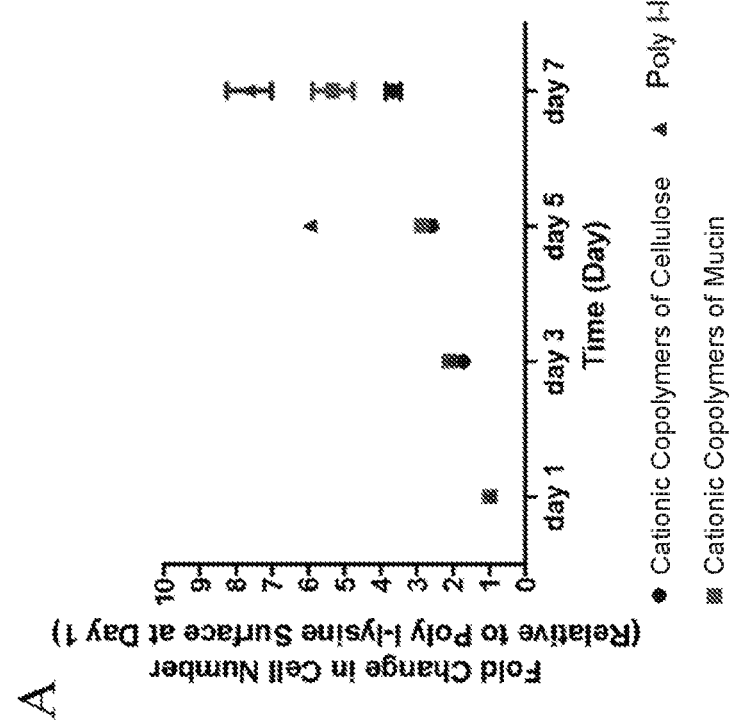

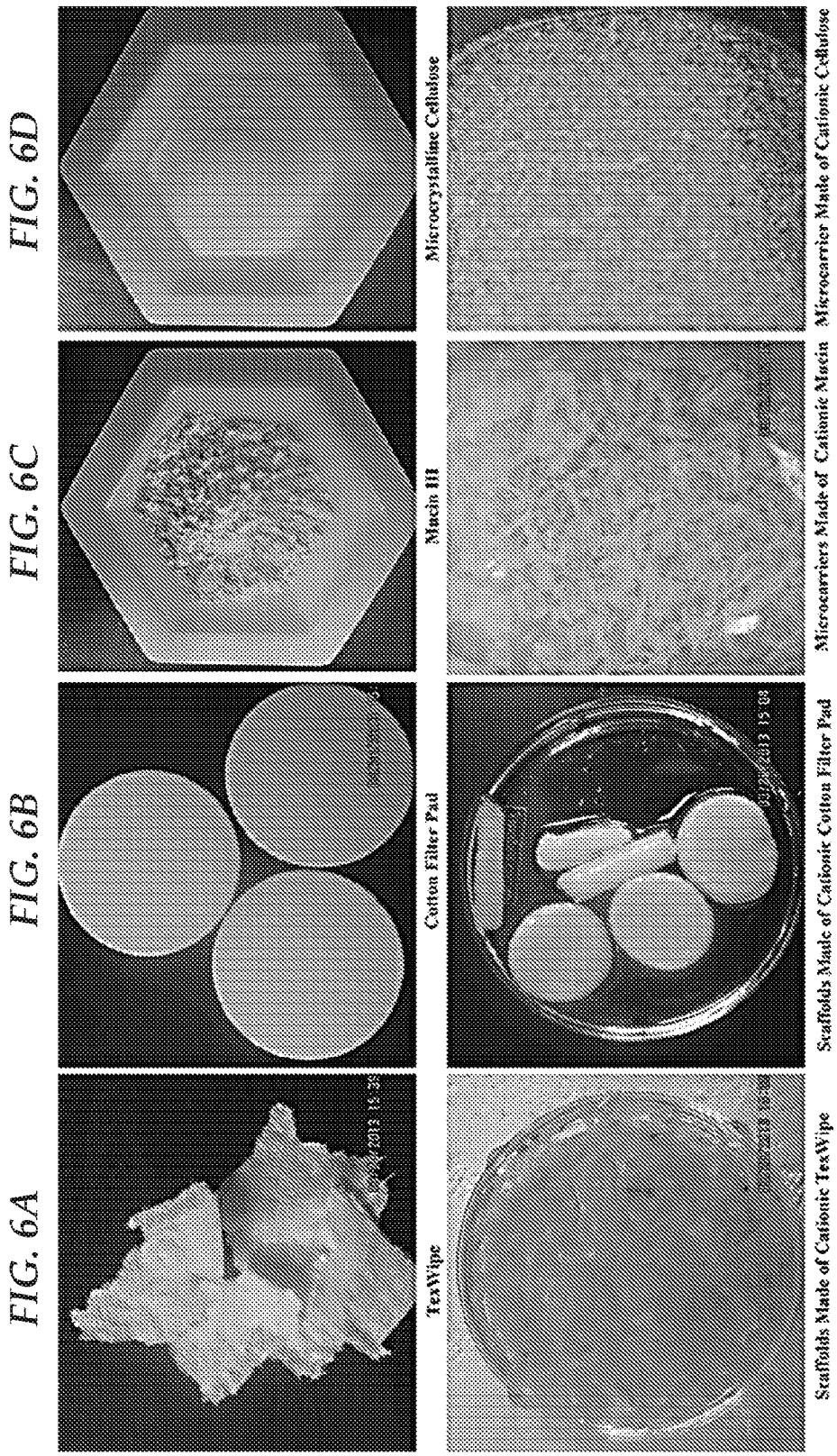

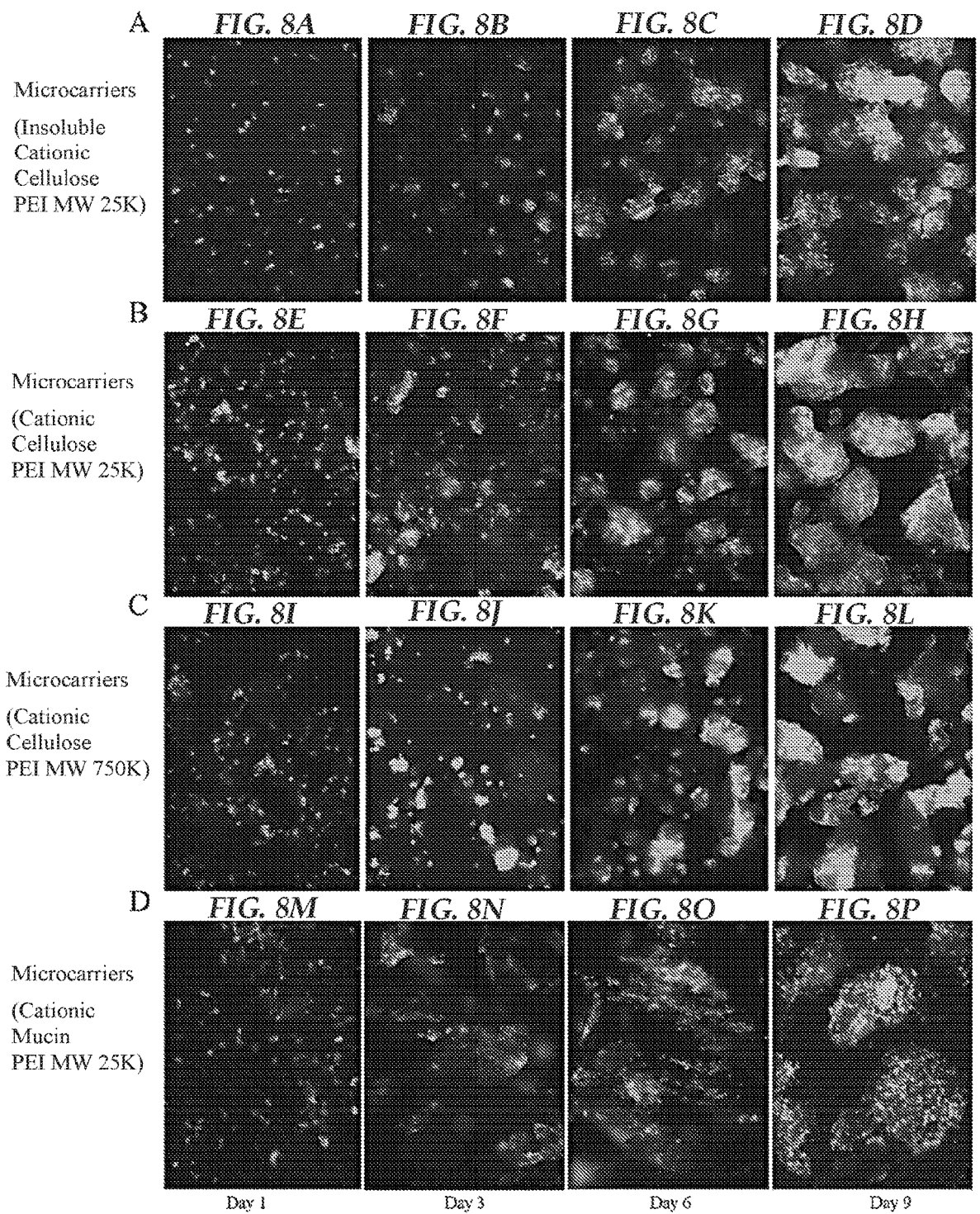

FIG. 9A  FIG. 9B
Microcarrier (Cationic Cellulose PEI MW 25K)
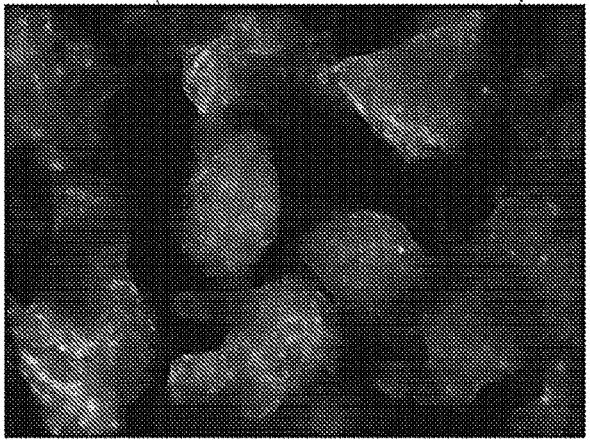
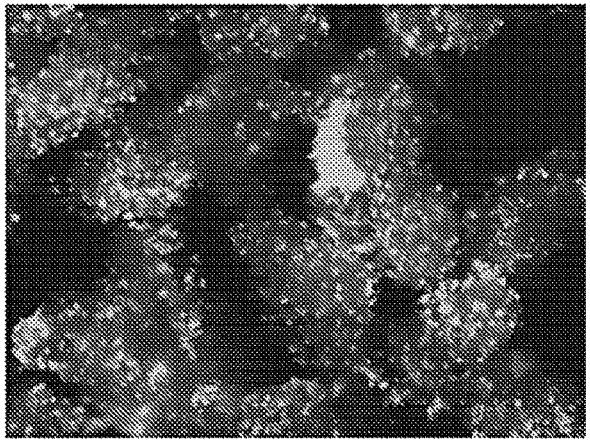
Microcarrier (Insoluble Cationic Cellulose PEI MW 25K)
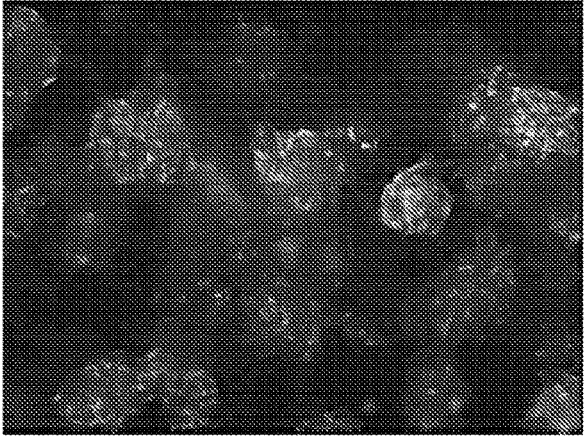
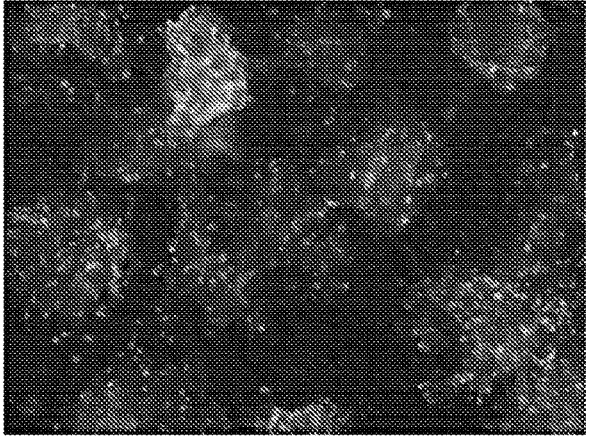
Day 9  Week 5
FIG. 9C  FIG. 9D

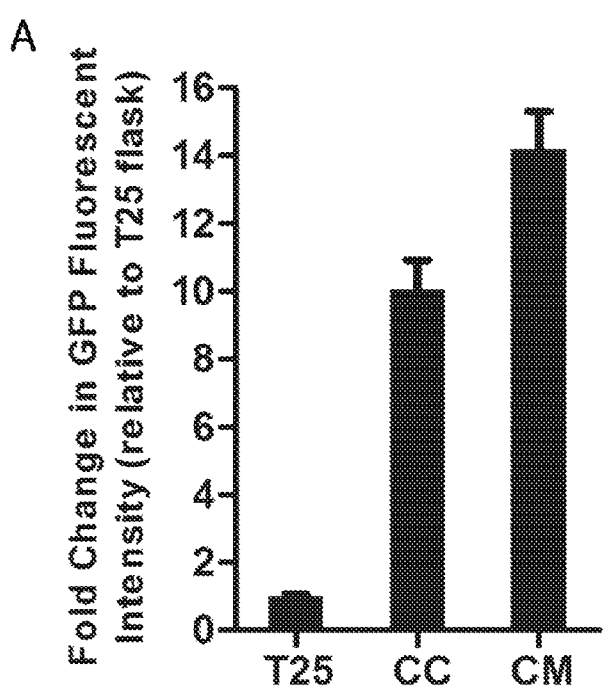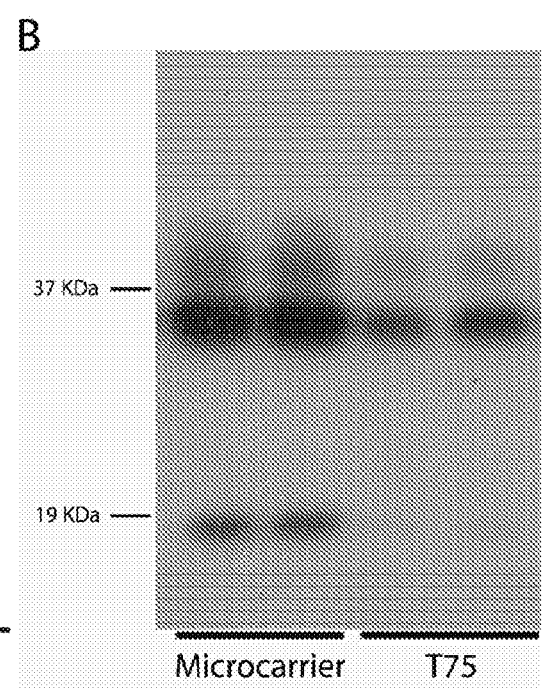
FIG. 10A
FIG. 10B

FIG. 11A
TexWipe
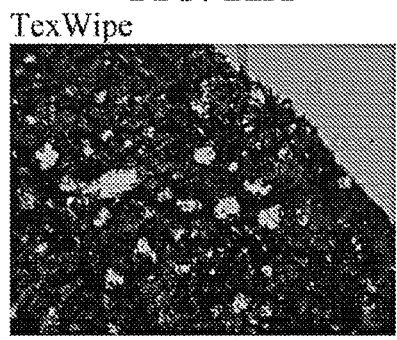
FIG. 11B
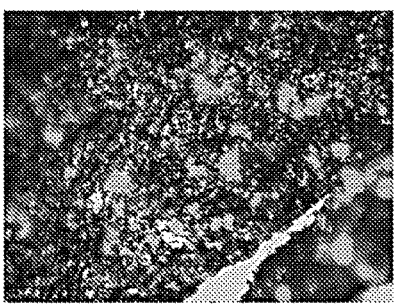
FIG. 11C
Cotton Filter Pad
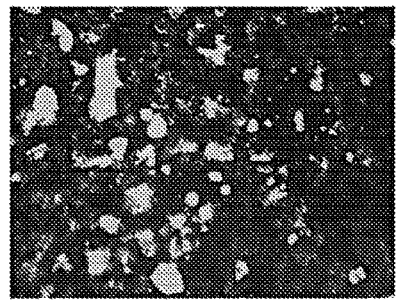
Untreated
FIG. 11D
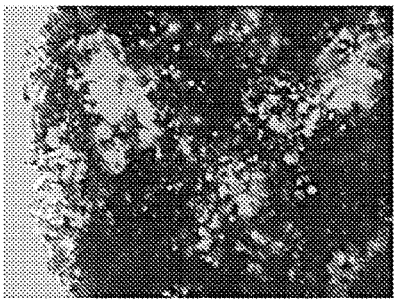
Coated
FIG. 11E
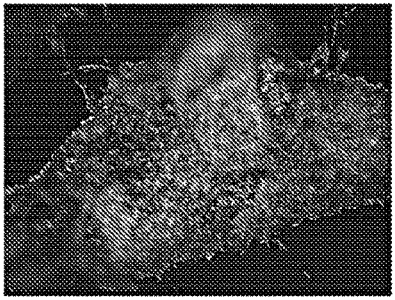
Transformed
FIG. 11F

MICROCARRIERS, MATRICES AND SCAFFOLDS FOR CULTURING MAMMALIAN CELLS AND METHODS OF MANUFACTURE

CROSS-REFERENCE TO RELATED APPLICATIONS

This application is a U.S. national phase application filed under 35 U.S.C. § 371 of International Application Number PCT/US2016/023248, filed Mar. 18, 2016, designating the United States, which claims benefit of the U.S. Provisional Application No. 62/136,241, filed Mar. 20, 2015.

FIELD

This disclosure generally relates to materials for culturing anchorage-dependent mammalian cells, and in particular, to carriers, matrices and scaffolds for high density growing of anchorage-dependent mammalian cells and methods of manufacture.

BACKGROUND

Culturing mammalian cells, especially human cells, is crucial in life science, pharmaceutical, and biotechnology research, as human cell cultures may be used to determine cell function and interactions and, for example, produce therapeutic cells, large quantities of proteins, and pathogens for the development of vaccines. Human gene products are commonly produced utilizing in vitro methods via bacterial, yeast, and insect gene expression systems. However, normal biological functionalities, activities, and metabolism of many human proteins are dependent on post-translational modification, such as glycosylation, ubiquitination, proteolytic cleavage, and disulfide bridges. These post-translational modifications can only be properly carried out in mammalian and sometimes only in human cells. In addition, proteins with a molecular weight above 30,000 Daltons (Da) generally cannot be expressed by micro-organisms. To produce such human proteins with their normal biological functions, mammalian cell expression systems may be the only suitable systems. Therefore, the ability to scale up the production of these proteins and the costs of such production are dependent on the yields of mammalian cell cultures, which are often proportional to the cell density of a cell culture.

Culturing anchorage-dependent mammalian cells in a three-dimensional (3-D) suspension model is one way of achieving high density culturing of cells. To achieve higher cell density growth, organotypic culture and microcarrier methods are used as the two major improved culture models. Although organotypic culture is real 3-D growth, the achievement of high density culture is still impeded by nutrient diffusion. The microcarrier method provides an anchor surface and allows culture of anchorage-dependent cells in a suspension model. However, cells typically grow as monolayers on the surface of the microcarriers suspended in the culture medium by gentle agitation, which is not true 3-D growth.

Most mammalian cells derived from solid tissues can only grow in an adherent mode. Affected by gravity, anchorage-dependent mammalian cells typically grow as monolayer on the lowest surface of the culture container. Since it is difficult to achieve high cell density growth in the conventional adherent growth mode, the cost of commercially produced pharmaceutical products by mammalian cell culture is very high. In addition, cells growing in a monolayer may be susceptible to damage resulting from collision of the cells during agitation of the culture medium or a bioreactor. In addition, such monolayer growth systems may be vulnerable to contamination, since they are directly exposed to the culture environment.

Furthermore, the surfaces of conventional cell growth microcarriers are often treated (e.g., by coating the carriers with collagen, fibronectin, laminin and Poly 1-lysine) to promote and enhance attachment of the cultured cells. The use of such coating materials and coating procedures significantly increases the cost of cell carriers and their related products.

Water soluble cationic copolymers presently have very limited application in the biomedical field due to their known high cytotoxicity. The cytotoxicity is known to result from the high charge density of soluble and mobile molecules in the solution.

Accordingly, systems for growing mammalian cells that overcome at least the above-discussed disadvantages are needed.

SUMMARY

Polysaccharide-polyamine copolymeric matrices or scaffolds and cationic copolymeric matrices or scaffolds are described herein and can be used as microcarriers for cells. The polysaccharide-polyamine copolymers, when protonated, can form cationic polymeric matrices having cationic sites. In one form, the covalently cross-linked copolymers provide a three-dimensional structure, especially when hydrated.

The polysaccharide-polyamine copolymers may be used as microcarriers for the culture of various types of cells such as primary cells, stem cells, cancer cells, immortalized cells, and the like. By one approach, the microcarriers are used for facilitating growth of anchorage-dependent mammalian cells. In one form, the microcarriers provided by the polysaccharide-polyamine copolymers described herein may provide a multiple layer, porous structure for cell growth. In addition, according to some forms, the pores of the microcarriers described herein are greater than 50 µm in diameter, advantageously allowing anchorage-dependent mammalian cells to grow on both the exterior surface and the interior surfaces of the cationic copolymeric particle microcarriers, similar to a 3-D growth pattern. This growth pattern facilitates nutrient infiltration during cell growth and may significantly increase the cell density per unit volume of the culture medium.

According to some forms, the 3-D open architecture of the microcarriers described herein may decrease the effects of typical disturbances to cell growth caused by agitation of the culturing medium and provide a stable environment for cell proliferation, including temperature, pH value, concentration of growth factors, and cytokines, decreasing and/or preventing cell damage known to occur from cell collisions caused by agitation such as stirring, shaking, or the like of the culture medium of the bioreactor. In addition, the multi-layer, porous structure of the microcarriers described herein may provide a stable microenvironment for the growth of cultured cells, decreasing chances for contamination, since the cells growing within the microcarriers are not directly exposed. In addition, the microcarriers described herein may be non-cytotoxic and are made from reusable, biocompatible, and environmentally friendly material. Further, since the surfaces of the microcarriers described herein may include positively charged sites, no extra treatment of the surface of these microcarriers is necessary for enhancing the attachment of cultured cells, allowing bioreactors utilizing the presently described microcarriers to maximize throughput while minimizing cost.

In one form, the resulting polysaccharide-polyamine copolymers belong to macroporous microcarriers containing both microporous and macroporous structures. Similar to other macroporous microcarriers, the polysaccharide-polyamine copolymers have many advantages over the monolayer surface-microcarriers. First, the macroporosity allow the cells easily access into the interior of the carrier and grow in three dimensions at high densities. In one form, the macroporous microcarriers not only protect the carried cells from the shear forces generated by a bioreactor, but also stabilize the micro-environment of cell growth. Second, in one form, the paracrine and autocrine growth hormones produced by the cells growing internal of the microcarrier decrease the need for external growth factors and allow the cells to create a micro-environment for long-term culture. Additionally, macroporous microcarriers may support good cell growth for a wide variety of cells including the anchorage-dependent cells, cells in suspension and semi-adherent cells. Further, several culture technologies can be used for macroporous microcarriers, including stirred, fluidized and packed bed reactors.

According to one form, the polysaccharide-polyamine copolymeric matrices are the result of the reaction of two pre-existing polymers or large molecules. In accordance with one form, the polysaccharide-polyamine copolymers may be considered di-block copolymers. In one form, the polysaccharide-polyamine copolymers are a reaction product of the selectively oxidized polysaccharides or the selective oxidized polysaccharide side chains having 2,3 di-aldehyde moieties and amino polymers having polyfunctional amino functionality reactive with the aldehyde moieties. The latter reaction product includes particulate cross-linked polymers which are the amino polysaccharide polymers, such as amino cellulosic polymers, having a three-dimensional structure. The amino functionality provides the cationic copolymers with cationic functionality when the amino functionality in the polysaccharide-polyamine copolymeric material is protonated.

In one aspect, the polysaccharide polymers are selected from the group consisting of selectively oxidized cellulose, selectively oxidized starch, selectively oxidized chitosan, selectively oxidized dextran, selectively oxidized glycogen, selectively oxidized chitin, and mixtures thereof. Selectively oxidized refers to having the hydroxyls at the C2 and C3 positions on a glucose unit of polysaccharide oxidized to aldehydes with concomitant cleavage of the C2-C3 bond where the oxidation will not produce more carboxyl groups than aldehyde groups and will not cleavage the polysaccharide chain.

In a very important aspect the polysaccharide polymers are oxidized polysaccharides selected from the group consisting of selectively oxidized cellulose, selectively oxidized chitosan, and mixtures thereof. As used herein, selectively oxidized cellulose, selectively oxidized starch, selectively oxidized chitosan, selectively oxidized dextran, selectively oxidized glycogen, selectively oxidized chitin means oxidized to the di-aldehyde. The latter selectively oxidized cellulose, selectively oxidized chitosan are important because they contain a β-1,4 glycosidic bond which cannot be digested by humans. The polymers such as cellulose, starch, chitosan, dextran, glycogen, and chitin are oxidized in an amount effective to provide the 2,3 di-aldehyde moiety which is reactive with the amino polymers polymers to permit the oxidized polysaccharide to react with the polyamino functional polymers which in turn provide the covalently cross-linked matrix or three-dimensional structure having amino functionality which can be protonated.

The materials discussed herein can be used for a variety of different uses. For example, the macroporous microcarriers can be used in industry to produce vaccines, therapeutic gene vectors, targeting proteins, monoclonal antibodies, and therapeutic cells. The macroporous microcarriers, polymeric matrices, and scaffolds can also be applied for the development of artificial tissues, the proteolytic enzyme-free subcultivation and cell transfer, and studies on cell communication, function, metabolism and differentiation.

BRIEF DESCRIPTION OF THE DRAWINGS

FIGS. 4A-4I are 3-D inverted fluorescence microscope images showing the growth and morphology of exemplary (human embryo kidney cell line HEK-293) cells overexpressing green fluorescent protein and grown on surfaces coated with poly 1-lysine (FIGS. 4A, 4D, and 4G), cationic copolymer of cellulose (FIGS. 4B, 4E, and 4H), and cationic copolymer of mucin (FIGS. 4C, 4F, and 4I);

FIG. 5A is a chart showing fold change in cell number over a period of 7 days and comparing the proliferation of cells growing on surfaces coated with poly 1-lysine, cationic copolymer of cellulose, and cationic copolymer of mucin;

FIG. 5B is a chart showing fold change in fluorescence intensity over a period of 7 days and comparing the exogenous protein expression of cells growing on surfaces coated with poly 1-lysine, cationic copolymer of cellulose, and cationic copolymer of mucin;

FIGS. 6A-6H show exemplary transformations of conventional starting materials (FIGS. 6A, 6C, 6E, and 6G) into exemplary scaffolds (FIGS. 6B and 6D) and microcarriers (FIGS. 6F and 6H) prepared according to the methods described herein;

FIGS. 8A-8P illustrate 3-D inverted fluorescence microscope images showing the growth and morphology of the HEK-293 cells overexpressing green fluorescent protein and grown for up to 9 days on exemplary microcarriers made according to the methods described herein;

FIGS. 9A-9D illustrate 3-D microscope images showing the growth and morphology of the HEK-293 cells overexpressing green fluorescent protein and grown for up to 9 days and 5 weeks on exemplary microcarriers made according to the methods described herein;

FIG. 10A shows a bar graph showing fold change in green fluorescent protein fluorescent intensity and comparing protein expression of cells growing on conventional 2-D surfaces and on exemplary microcarriers made according to the methods described herein;

FIG. 10B shows a Western Blot analysis illustrating erythropoietin expression of cells growing on conventional 2-D surfaces and on exemplary microcarriers made according to the methods described herein;

FIGS. 11A-11F are 3-D microscope images showing the growth and morphology of the HEK-293 cells overexpressing green fluorescent protein and grown on untreated surfaces as well as on coated, and transformed scaffolds including the cationic copolymers as described herein;

DETAILED DESCRIPTION

Figure 1:
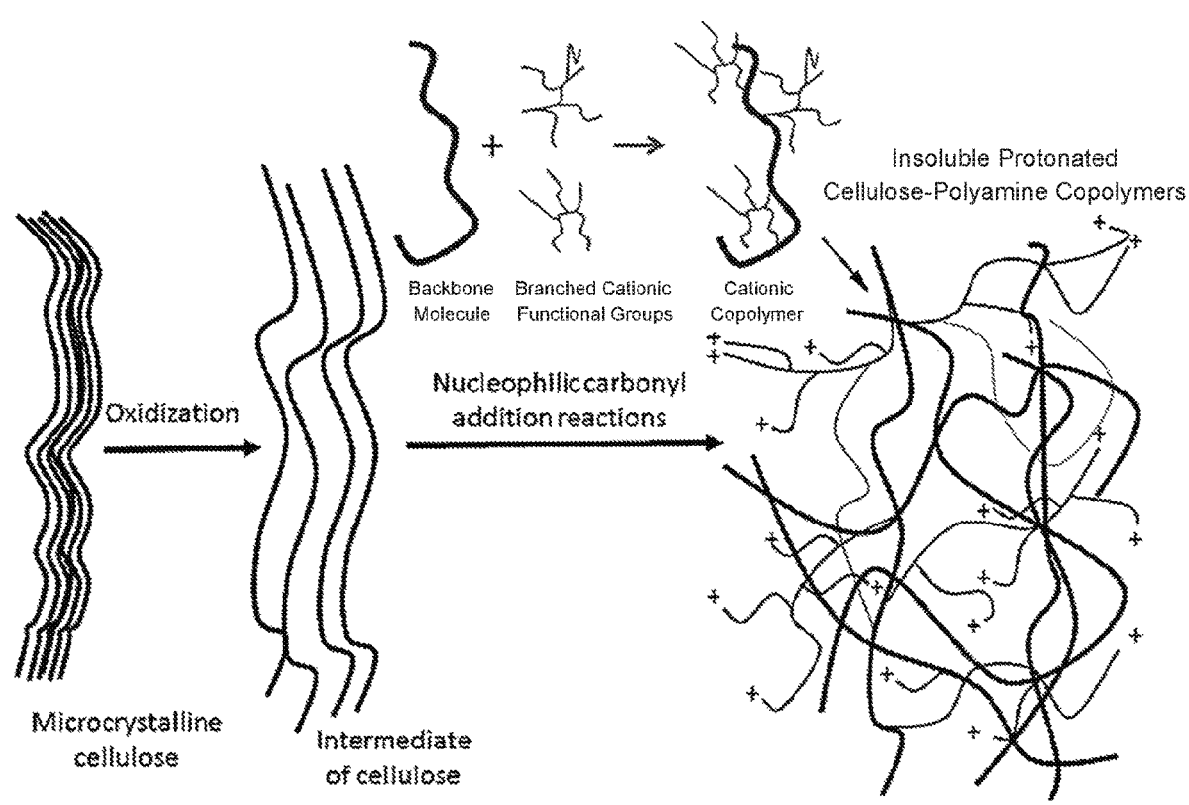
FIG. 1 is a schematic illustration of synthesis of exemplary polyamine cellulosic copolymers using a cellulose backbone.

In one form, the covalently cross-linked copolymers are polysaccharide-polyamine copolymers that generally include two components, namely, a backbone molecule and a functional cationic polymer group covalently cross-linked to the backbone molecule. In one approach, stable covalent bonds formed between a water soluble cationic polymer and a large polymeric molecule provide a water insoluble cationic copolymer. Such immobilization of the water soluble cationic polymer advantageously reduces or eliminates the cytotoxicity of the cationic polymer in cell culture applications.

The polysaccharide-polyamine copolymers can be used as cell carriers, matrices and scaffolds for culturing anchorage-dependent mammalian cells, advantageously providing for significantly higher density cell growth as compared to existing cell culture microcarrier systems. The polysaccharide-polyamine copolymers may be used as coating materials applied to a variety of surfaces, such as cell culture tubes, plates, or other materials, including paper, glass, metal, and ceramics, for culturing mammalian cells, and advantageously provide a porous structure suitable for culturing anchorage-dependent mammalian cells. The polysaccharide-polyamine copolymers may also be provided in particle form and used as a cell carrier to culture mammalian cells in a three-dimensional suspension model. Exemplary methods for producing such polysaccharide-polyamine copolymers and cell culture-supporting surfaces including such insoluble cationic copolymers and some possible applications of the cationic copolymer-based as cell carriers, matrices and scaffolds are also described.

In one form, the cross-linked copolymers provide a three-dimensional structure, especially when hydrated. In some forms, the polysaccharide-polyamine copolymer can be even more specifically characterized as a polyamine-cellulosic copolymer that includes cellulose derived materials forming the polysaccharide component.

In one approach, a method of producing polysaccharide-polyamine copolymers as described herein includes an oxidation reaction and a nucleophilic carbonyl addition reaction. In one approach, the oxidation reaction may involve oxidation of a saccharide, by one approach, a polysaccharide such as microcrystalline cellulose, amylopectin, starch, chitosan, chitin, dextran, glycogen, or the like. In another approach, the oxidation reaction may involve oxidation of a saccharide-containing glycoprotein, such as mucin or the like. The polymer may be produced having differing levels of amines and/or cationic sites. Different types of mammalian cells require various strength of the charge carried by the surface to which the cell is attached to facilitate the attachment and growth of the cells. Microcarriers made of copolymers with different densities of cationic charge-carriers can be applied for culturing various types of cells with specific charge requirement.

In one aspect, polysaccharide polymer and glycoproteins are selected from the group consisting of selectively oxidized cellulose, selectively oxidized starch, selectively oxidized chitosan, selectively oxidized dextran, selectively oxidized glycogen, selectively oxidized chitin, and selectively oxidized mucin mixtures thereof. Selectively oxidized refers to having the hydroxyls at the C2 and C3 positions on a glucose unit of polysaccharide from di-aldehyde oxidized with concomitant cleavage of the C2-C3 bond where the oxidation will not produce more carboxyl groups than aldehyde groups and will not cleavage the polysaccharide chain.

In one aspect the amino polymers are branched polymer or dendrimers which are macromolecular amines that have a core or center which includes amine groups and branches that include these functional groups which may be formed through a series of iterative reactions starting with the functional groups at the core or center to provide a highly branched amine polymer. In one aspect, the dendrimer molecule may be round or substantially round or have a three-dimensional morphology which is spherical or has an outer perimeter which is curvilinear or bounded by curved lines.

The amino polymers cross-link the polysaccharide polymers or glycoproteins, such as oxidized cellulose and mucin (having the di-aldehyde moieties) to provide the three-dimensional structure of polysaccharide-derived "backbones" and glycoprotein derived "backbones" where multiple polysaccharide chains are linked with multiple chains of the amino polymers. These polysaccharide polymers and glycoproteins are pre-existing polymers which are "blocks" or "backbones" linked together by pre-existing amino polymers which also are discrete amino blocks. In one form, the polysaccharide-polyamine copolymers may be considered to be di-block copolymers. The linked backbones are bonded together as the covalent cross-linking products of the amine polymers (which form cross-linking blocks) and the selectively oxidized polysaccharide or selectively oxidized glycoprotein to provide cross-linked block copolymer and copolymeric matrices with high percent of amine content which may be protonated.

Cellulose and chitosan contain β-1, 4-glycosidic bonds which cannot be digested by mammals. Starch, dextran and glycogen contain β-1, 6-glycosidic bonds and are digestible by humans. Without wishing to be limited by theory, cellulose and similar polysaccharides may provide for longer term cell growth than mucin and similar glycoproteins. Cellulose is generally metabolically inert because mammalian cells typically do not consume cellulose as they are growing on it, while mucin is generally considered to be susceptible to bacterial digestion.

The amino polymers cross-link the polysaccharide polymers or glycoproteins, to provide the three-dimensional structure of polysaccharide-derived "backbones" and glycol-protein derived "backbones" where multiple polysaccharide chains are linked with multiple chains of the amino polymers. These polysaccharide polymers and glycoproteins are pre-existing polymers which are "blocks" or "backbones" linked together by pre-existing amino polymers which also are discrete amino blocks. In one form, the polysaccharide-polyamine copolymers may be considered to be di-block copolymers. The linked backbones are bonded together as the covalent cross-linking products of the amine polymers (which form cross-linking blocks) and the selectively oxidized polysaccharide or selectively oxidized glycoprotein to provide cross-linked block copolymer and copolymeric matrices with high percent of amine content which may be protonated.

The covalently cross-linked copolymers may be prepared in a variety of manners. In one form, the preparation takes place in three steps. First, through an oxidation reaction, abundant aldehyde groups are generated on polysaccharides or polysaccharide side chains by selectively oxidizing the hydroxyl groups on C2 and C3 of the glucose units. In one form, selective oxidation generally means to oxidize the hydroxyl groups in the C2 and C3 positions on a glucose unit of polysaccharide to the corresponding aldehydes with the concomitant cleavage of the C2-C3 bond. Such oxidization will not produce more carboxyl groups than aldehyde groups and cause cleavage of the polysaccharide chain. A carboxyl group cannot covalently cross-link amine polymers under the conditions of the oxidation reaction and that if formed carboxylic the carboxyl groups will undesirably form carboxylic acid in an aqueous environment. Further if formed, carboxylic acid will carry a negative charge which will undesirably interfere with the cationic charges formed when the amine groups are protonated.

The aldehyde groups generated by selective oxidation of the polysaccharides react with primary amines of amino polymers to form imine derivatives, the intermediate polysaccharide-polyamine copolymers with unstable carbon-nitrogen double bonds. In one form, these are considered di-block copolymers. Next, a reduction reaction is carried out to convert the carbon-nitrogen double bonds of the imines into the carbon-nitrogen single bonds of amines in order to produce the stable polysaccharide-polyamine copolymers.

According to one form, the polysaccharide-polyamine copolymeric matrices are the result of the reaction of two pre-existing polymers or large molecules. In accordance with one form, the polysaccharide-polyamine copolymers may be considered di-block copolymers. In one form, the polysaccharide-polyamine copolymers are a reaction product of oxidized polysaccharides or oxidized glycoproteins having 2,3 di-aldehyde moieties and amino polymers having polyfunctional amino functionality reactive with the aldehyde moieties. The latter reaction product includes particulate cross-linked copolymers which are the polysaccharide-polyamine copolymers, such as cellulose-polyamine copolymers, having a three-dimensional structure. The amino functionality provides the cationic copolymers with cationic functionality when the amino functionality in the polysaccharide-polyamine copolymeric material is protonated.

An intermediate polymer resulting from the above-discussed oxidation reaction may have the following general formula:

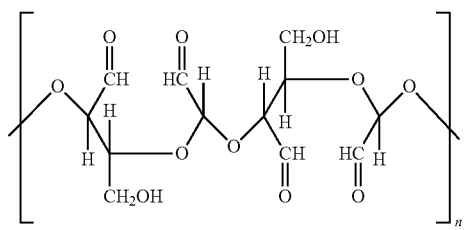

Figure 12:
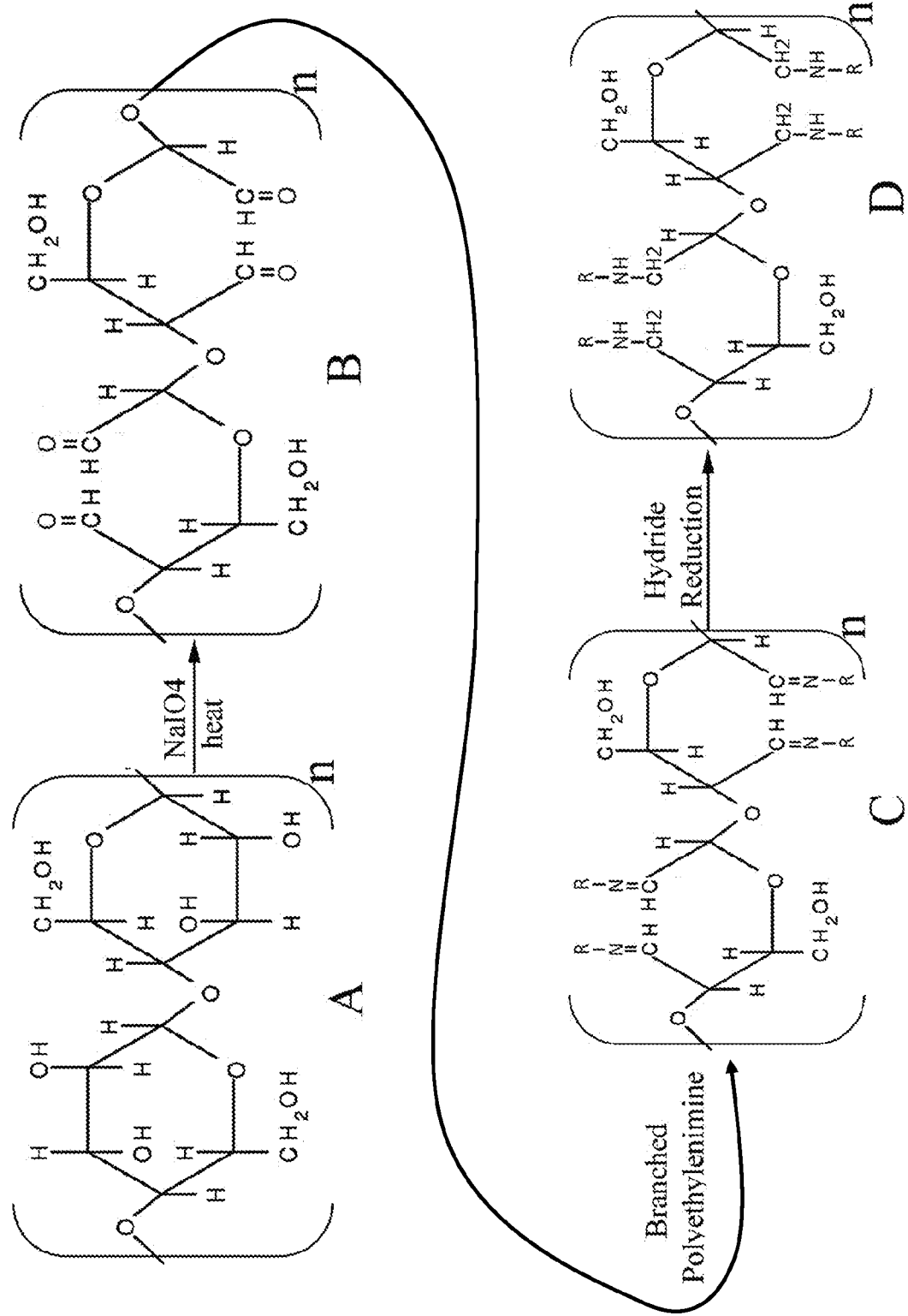
FIG. 12 is a schematic illustration of a method of obtaining an exemplary copolymer from cellulose.
Figure 13:
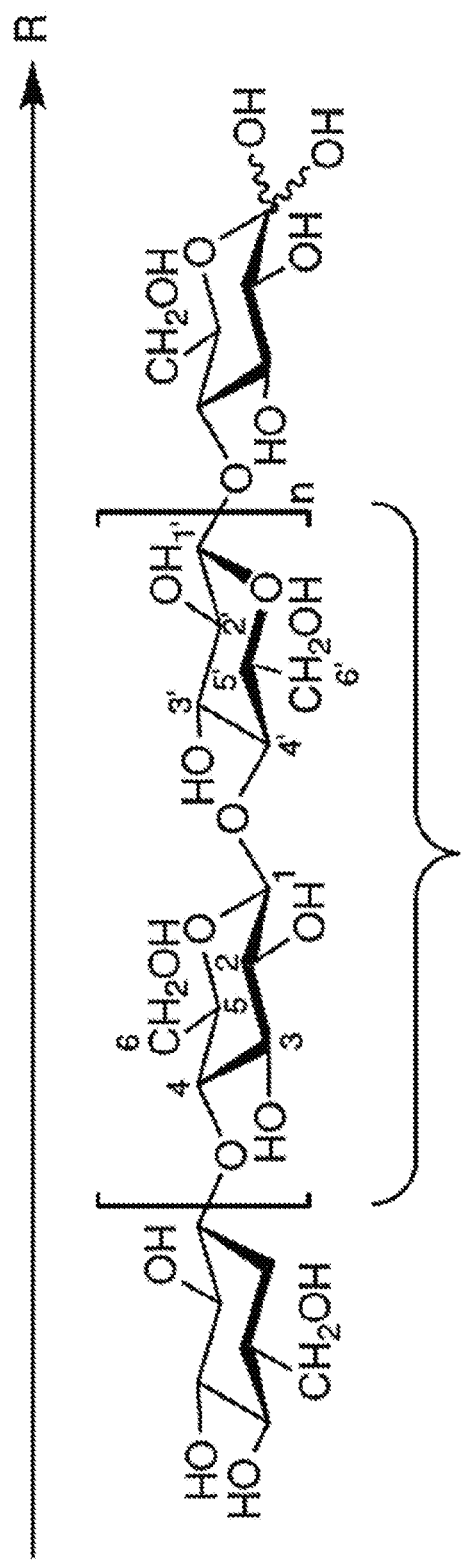
FIG. 13 is a general molecular structure of cellulose.

Reaction 1, as shown in FIG. 12, shows a schematic illustration of a method of obtaining an exemplary polymer from cellulose. Cellulose is a naturally occurring polymer including glucose units interconnected by β-1, 4-glycosidic bonds. The molecular structure of cellulose, which forms a backbone of the cellulose derivitised polymer is generally represented in FIG. 13.

As seen in FIG. 12, a polysaccharide such as microcrystalline cellulose may be oxidized to form an intermediate of cellulose. In one approach, carbonyl group-enriched intermediates such as aldehydes are generated by the oxidization of the polysaccharide backbone. In particular, reactive aldehyde groups may be created by the opening of multiple glucose units along the polysaccharide backbone.

In FIG. 12, formula "A" generally represents cellulose, which may be any commercially available cellulose and formula "B" generally represents 2,3-dialdehyde cellulose that results from the oxidation of cellulose. As can be in FIG. 12, the 2, 3-dialdehyde cellulose is a linear polymer with a structure similar to cellulose and includes one or more (and in the illustrated approach, two) reactive aldehyde groups per glucose unit. By one approach, cellulose may be pre-treated with sulfuric acid to reduced crystallinity degree and size.

While the exemplary chemical reaction in FIG. 12 utilizes sodium periodate ($NaIO_4$) as an oxidizing agent, it will be appreciated that the oxidation of cellulose may be alternatively catalyzed by periodic acid, potassium periodate, or other cationic derivitised and salts of periodic acid, or the like. Other oxidizing agents include chlorine, hydrogen peroxide, peracetic acid, chlorine dioxide, nitrogen dioxide, persulfates, permanganate, dichromate-sulfuric acid, hypochlorous acid, hypohalites or periodates and a variety of metal catalysts. Oxidized polysaccharides including oxidized cellulose may contain carboxylic acid, aldehyde, and/or ketone groups, in addition to the original hydroxyl groups of the starting material, depending on the nature of the oxidant and reaction conditions.

Periodates are a unique form of oxidants. Periodate-mediated oxidation of polysaccharides including cellulose is known to selectively oxidize the hydroxyl groups in the C2 and C3 positions on a glucose unit of polysaccharide to the corresponding aldehydes with the concomitant cleavage of the C2-C3 bond and is one of the most potent methods for polysaccharides modification. But other oxidants will produce more carboxyl groups than aldehyde groups and cause cleavage of chain of polysaccharides. The carboxyl group cannot covalently cross-link amine polymer under the reaction condition as described. Additionally, it will ionize and become carboxylic acid in aqueous solution. The carboxylic acid carries the negative charges and disturbs the cationic function of the copolymers.

In one approach, the polymer intermediate formed as a result of the oxidation of polysaccharides as described above may then be subjected to nucleophilic carbonyl addition (e.g., hydride reduction) reactions with one or more branched cationic functional groups such as amino/imine polymers. Generally, polyfunctional primary amine-containing molecules can cross-link with the aldehyde-containing oligosaccharide derived from polysaccharides such as cellulose and the like or glycoproteins and the like. By one approach, a large molecular weight polyfunctional primary amine agent may be used to provide for the formation of a high density of cationic sites on the derivitised saccharide when later protonated. For most approaches, any polyamine (both the linear and branched) containing multiple primary amines can be used as a nucleophilic reagent.

The above-described reaction of a high molecular weight polyamine such as polyethyleneimine with an aldehyde group-containing saccharide derivitised of cellulose results in formation of stable covalent bonds between the water soluble cationic copolymer and a cellulose backbone molecule, thereby providing a water insoluble cationic polymer generally represented by formula "C" above and discussed in more detail below. In the above-illustrated exemplary reaction, the cellulose intermediate-containing reactive aldehyde groups formed as a result of the oxidation of cellulose with sodium periodate is subjected to a nucleophilic carbonyl addition reaction, and in this example, a hydride reduction reaction, with a cationic functional polymer such as polyethyleneimine to derive an exemplary insoluble cationic cellulose derivitised copolymer generally represented by formula "C."

While the above-illustrated exemplary reaction utilizes polyethyleneimine as the nucleophilic agent, other exemplary cationic copolymers may be usable as nucleophiles in the reaction with the above-described intermediates of cellulose including reactive aldehyde groups. Some exemplary cationic functional polymers include, for example, poly (allylamine), poly(amidoamine), polypropylenimine tetramine and the like. Polyethyleneimine, poly(allylamine) and polypropylenimine tetramine are synthetic polyamine containing polymers which are generally considered as branched polymers or dendrimers. Polypeptides generally contain high percentages of amino acids including arginine, lysine, asparagine and glutamine, and certain polypeptides, may be utilized instead of the synthetic polyamines in the reactions described herein.

In addition, branched or macrocyclic polyamines as described in International Publication No. WO 2014/029888, incorporated by reference herein in its entirety, may be suitable for the reactions as described herein. Furthermore, some exemplary linear polyamines suitable for the reactions described herein are listed below:

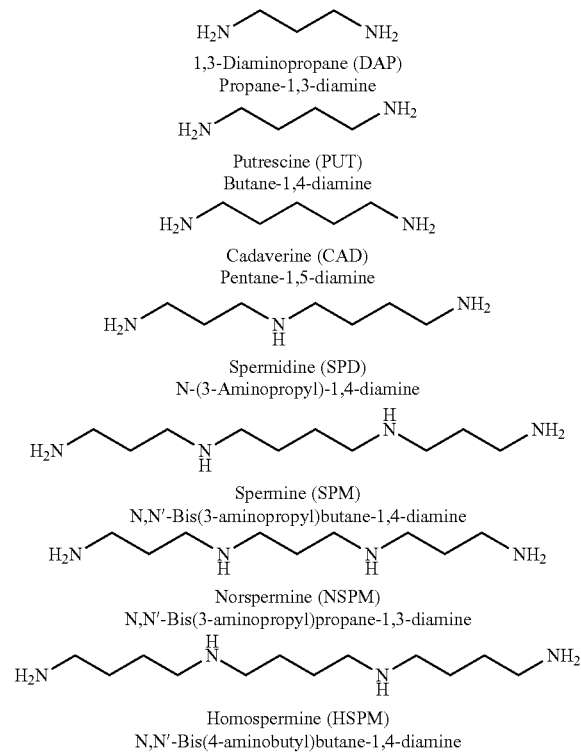

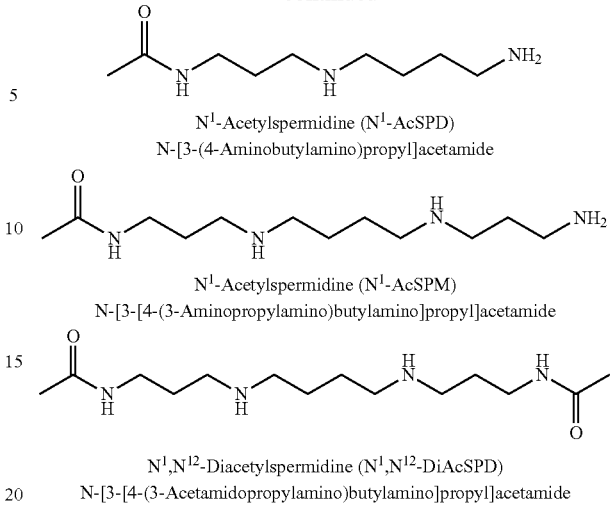

After the above-described reaction of the polysaccharide derivitised with a nucleophilic agent, the resulting product may be dried by lyophilization, evaporation or precipitation as long as the process does not collapse the interior three-dimensional structure of the particles. By one approach, cationic copolymer material of uniform particle size may be achieved by screening the dried material through a suitable mesh, such as having a median particle size from about 100 m to about 10 mm in size.

By one approach, the amino density of the resulting cationic copolymers is also controlled by the degree of polymerization, size of the nucleophile and the relative ratio of the polysaccharide substrate backbone and nucleophile. As used in this application, charge density refers to the number of the primary, secondary, and tertiary ammonium cations within the cationic copolymer. In an important aspect the branched polyamine has a nitrogen content of at least 24.5 wt. % based upon the weight of the branched polyamine which is effective to provide the polysaccharide-polyamine copolymeric material when protonated (which results in the cationic copolymer matrix) with a nitrogen content of no more than 30 wt. %, and preferably in the range of 0.5-20 wt. %, based upon the weight of the cationic material.

The ranges may be qualitatively described as low, moderate, and high based on the molar ratios of the aldehyde-containing saccharide derivitised and the functional primary amine nucleophile. In one approach, the aldehyde content and the primary amine content of the reactants are determined by quantitative titrimetry, while the NH2+ content of the final product is determined by Nuclear Magnetic Resonance Spectroscopy (NMR).

The physical characteristics of the polysaccharide-polyamine copolymer resulting from the above-described oxidation and nucleophilic carbonyl addition reaction may be controlled by manipulating the conditions of the above-described reaction, for example, by varying the relative ratios of the substrate backbone and nucleophile, varying the types of functional groups used for reaction with the substrate backbone, and/or varying the time, pH, and/or temperature of the reaction. For example, increasing the temperature at which the reaction is carried out can lead to a corresponding increase in the size of the resulting polysaccharide-polyamine copolymer. In another example, increasing the reaction time can lead to a corresponding increase in the size of the resulting polysaccharide-polyamine copolymer. In yet another example, increasing the pH of the reaction conditions can lead to a corresponding increase in the size of the resulting polysaccharide-polyamine copolymer. In still yet another example, the size of the resulting polysaccharide-polyamine copolymer product can be controlled via selection of the molecular weight and ratios of the two major reactants, namely, the derivative (poly)saccharide (e.g., 2,3-dialdehyde cellulose) and the polyamine nucleophile (e.g., polyethyleneimine).

In one approach, poly(allylamine) (PLA) with an average molecular weight of about 15,000 Da to about 900,000 Da or polyethyleneimine (PEI) with an average molecular weight of about 25,000 Da to about 750,000 Da can be used. For example, PLA with an average molecular weight of approximately 15,000 Da, 17,000 Da, 65,000 Da, or 900,000 Da, or PEI with an average molecular weight of approximately 25,000 Da or 750,000 Da obtained from Sigma-Aldrich may be used. The ratio of the polysaccharide backbone component (e.g., cellulose) to the cationic site forming functional polymer (e.g., polyethyleneimine) used in the reaction may depend upon the molecular weight of the cationic site forming functional polymer. For example, for PEI and PLA with molecular weight from about 15,000 Da to about 25,000 Da, the ratio of the derivitised cellulose to polyamine may range from about 1:1 to about 1:8. In one approach, when PEI and PLA with molecular weight ranging from about 65,000 to about 750,000 is used, the ratio of the derivitised cellulose to polyamine ranges from about 1:5 to about 1:20.

However, it has been found that not all of these cationic copolymers may be suitable for composing of cell microcarriers, since these copolymers become strongly positively charged materials through protonation and show noticeable cytotoxicity. For example, for PEI and PLA with molecular weight from about 15,000 Da to about 25,000 Da, the ratio of the derivitised cellulose to polyamine may range from about 50:1 to about 1:8. In one form, only copolymers within range from about 50:1 to about 1:1 are suitable for composing macrocarriers. In one approach, when PEI and PLA with molecular weight ranging from about 65,000 to about 750,000 is used, the ratio of the derivitised cellulose to polyamine ranges from about 10:1 to about 1:20. But only copolymers within range from about 10:1 to about 1:5 are suitable for composing macrocarriers.

The particle size of the insoluble cationic copolymer product may be regulated by coupling the cross-linking polyfunctional primary amines (e.g., polyethyleneimine) with the oxidized polysaccharide derivative (2, 3-dialdehyde cellulose) and selectively oxidized glycoproteins having low, intermediate, and very high molecular weights (e.g., ranging from about 15,000 Da to 750,000 Da) to obtain particles ranging from about 10 nm to about 5 mm.

By one approach, the nanoparticle sized cationic copolymer particles may be used as transfection agents, the millimeter sized (and larger) cationic copolymer particles may be used as 3-D growth carriers, and the micron-sized cationic copolymer particles may be used for coating on cell culture plates, plastic tubes, and generally may coat any surface suitable for cell growth.

The cationic copolymers obtainable by the above-described reactions may be used as microcarriers for the culture of various types of cells such as primary cells, stem cells, cancer cells, immortalized cells, and the like. By one approach, the microcarriers are used for facilitating growth of anchorage-dependent mammalian cells. While conventional microcarriers are typically solid beads that permit the cells to grow in a monolayer on the surface of the beads, the surfaces of the existing microcarriers generally need to be treated (e.g., by an attachment protein) to enhance the attachment of cultured cells to the microcarriers. In addition, while conventional microcarriers are often used for cultivating cells in a suspended state by proliferating cells in a single layer on the surface of the microcarriers, the microcarriers provided by the cationic copolymers described herein advantageously provide a multiple layer, porous structure for cell growth. In addition, while some known microcarriers have an average pore size of about 30 µm, the pores of the microcarriers described herein are greater than 50 µm in diameter, advantageously allowing anchorage-dependent mammalian cells to grow on both the exterior surface and the interior surfaces of the cationic polymer particle microcarriers, similar to a 3-D growth pattern. This growth pattern advantageously facilitates nutrient infiltration during cell growth and advantageously significantly increases the cell density per unit volume of the culture medium.

Without wishing to be limited by theory, the 3-D open architecture of the microcarriers described herein advantageously decreases the effects of typical disturbances to cell growth caused by agitation of the culturing medium and provides a stable environment for cell proliferation, including temperature, pH value, concentration of growth factors, and cytokines, decreasing and/or preventing cell damage known to occur from cell collisions caused by agitation such as stirring, shaking, or the like of the culture medium of the bioreactor. In addition, the multi-layer, porous structure of the microcarriers described herein provides a stable microenvironment for the growth of cultured cells, advantageously decreasing chances for contamination, since the cells growing within the microcarriers are not directly exposed. In addition, the microcarriers described herein are non-cytotoxic and are made from reusable, biocompatible, and environmentally friendly material. Further, since the surfaces of the microcarriers described herein include positively charged sites, no extra treatment of the surface of these microcarriers is necessary for enhancing the attachment of cultured cells, allowing bioreactors utilizing the presently described microcarriers to maximize throughput while minimizing cost.

Figure 2A:
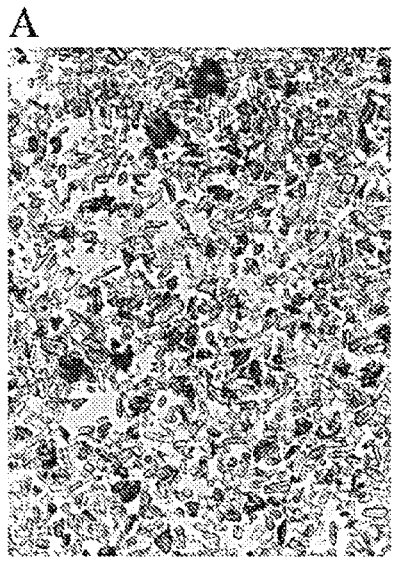
FIGS. 2A-2F are confocal microscopy images illustrating the morphology and structure of exemplary cationic copolymers of cellulose and mucin.
Figure 2B:
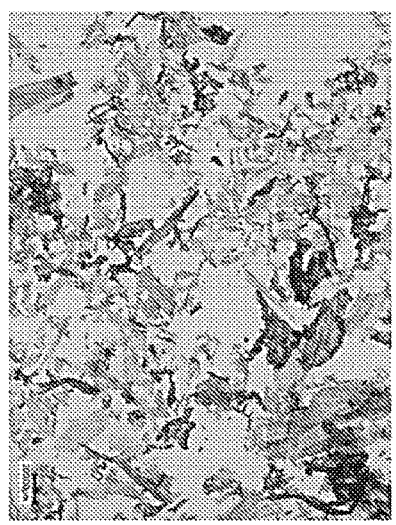
Figure 2C:
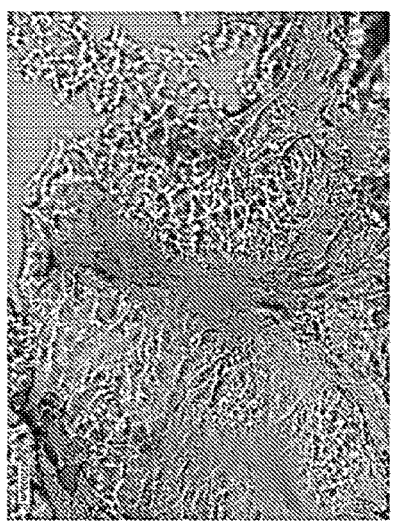
Figure 2D:
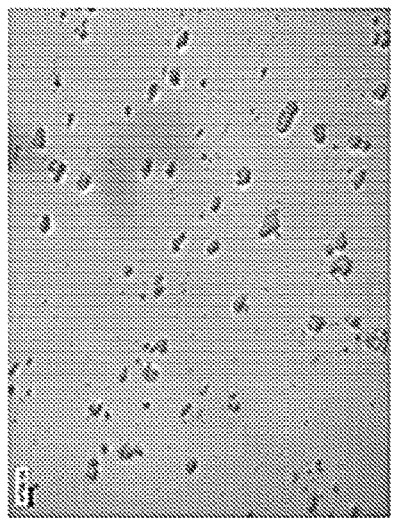
Figure 2E:
Figure 2F:
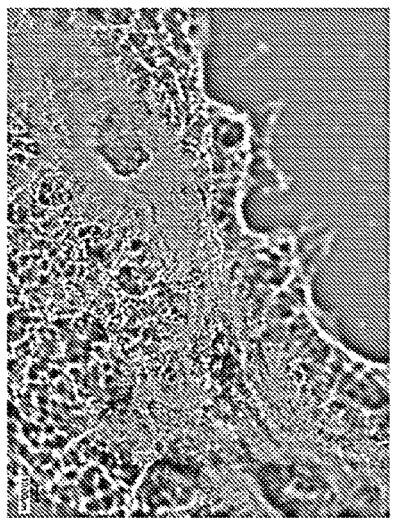

FIGS. 2A-2F show images generated by a Keyence VHX-2000 series Digital Microscope and depict the morphology and structure of some exemplary cationic copolymer of cellulose and cationic copolymer of mucin obtainable by the oxidation-nucleophilic addition reaction as described above. For example, FIG. 2A shows the morphology and structure of microcrystalline cellulose, while FIGS. 2B and 2C show the morphology and structure of the water insoluble cationic copolymer of cellulose, with FIG. 2B depicting a 20× image of the cationic copolymer of cellulose stained with Eosin (an anionic dye) and FIG. 2C depicting the cationic copolymer of cellulose at 400× without Eosin staining. FIGS. 2D-2F show similar images but for mucin instead of microcrystalline cellulose. A comparison of FIG. 2A to FIGS. 2B and 2C and a comparison of FIG. 2D to FIGS. 2E and 2F shows that the cationic copolymers of cellulose and mucin, respectively, have significant morphological differences as compared to the native cellulose and mucin. For example, the cationic copolymer of cellulose and cationic copolymer of mucin bind with Eosin while native cellulose and native mucin would not. In addition, FIGS. 2C and 2F show that the cationic copolymer of cellulose and cationic copolymer of mucin, respectively, have a multiple layer porous structure unlike native cellulose and mucin.

FIGS. 4A-4I depict images obtained with a 3-D microscope and depicting the morphology of the surfaces coated with various materials and investigating the growth of the cells on coated surfaces. In one approach, untreated polystyrene surfaces of dishes were coated with poly 1-lysine, cationic copolymer of cellulose, or cationic copolymer of mucin. The coated surfaces were then stained with eosin and examined with a 3-D microscope, with the results being shown in FIGS. 4A-4C. By one approach, human embryo kidney cell line (HEK-293) overexpressing green fluorescent protein (GFP) was seeded and grown on the coated surface, and the morphology and growth of cells was investigated with fluorescent microscopy and phase contrast microscopy at 3 days (results shown in FIGS. 4D-4F) and at 7 days (results shown in FIGS. 4G-4I). As can be seen in FIGS. 4A-4C, the cationic copolymer of cellulose and the cationic copolymer of mucin form a porous coating layer on the polystyrene surface and HEK-293 cells attach and grow on the coated surface. As can be seen in FIGS. 4D-4I, stronger GFP fluorescent intensity was obtained from the cells growing on the surfaces coated with the cationic copolymers than the cells growing on poly 1-lysine treated surface, indicating that cells growing on the surfaces coated with the cationic copolymers are much healthy than cells growing on poly 1-lysine treated surface.

Figure 3A:
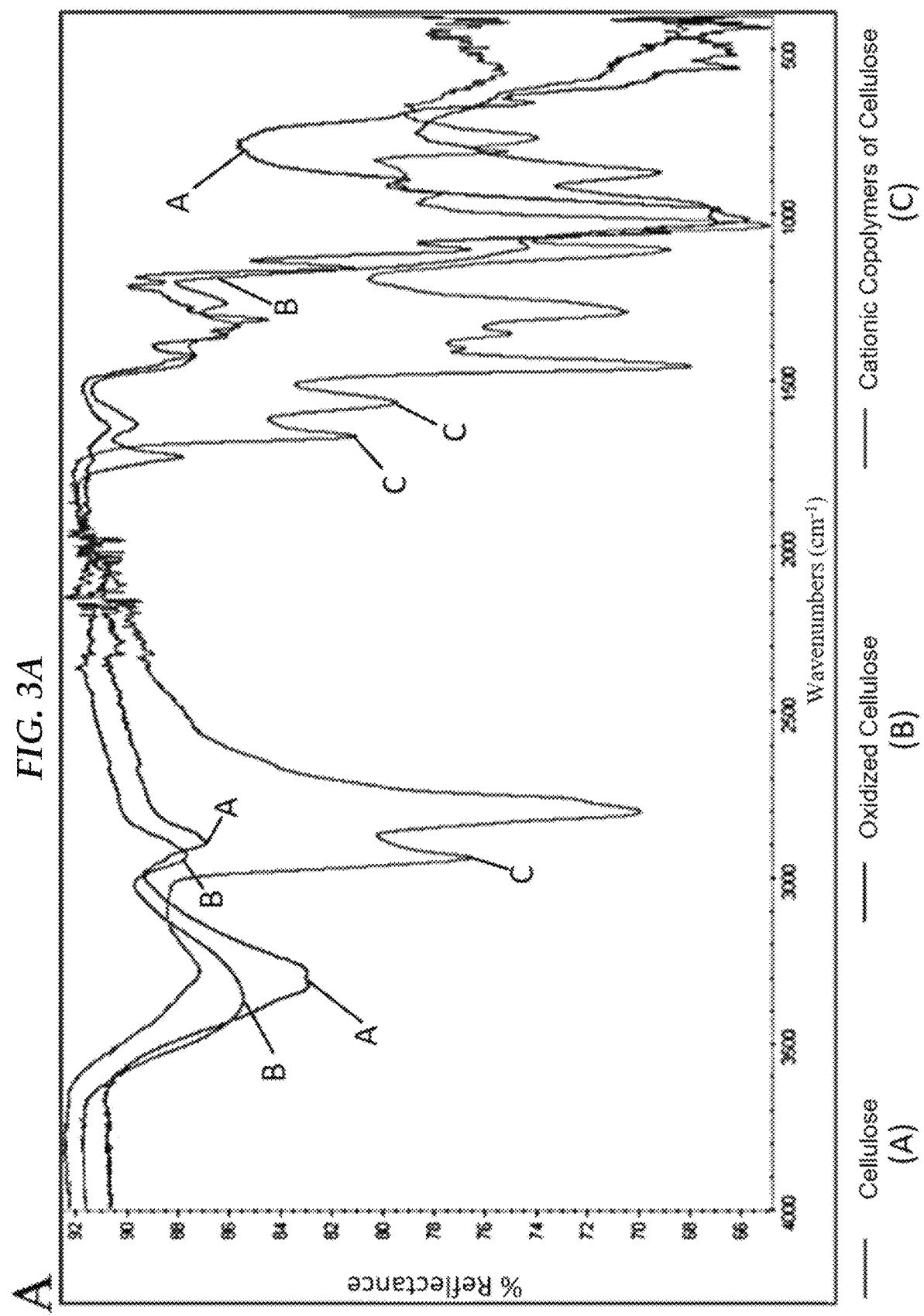
FIGS. 3A and 3B show Fourier transform infrared spectra characterizing native cellulose/mucin, oxidized cellulose/mucin, and cationic copolymers of cellulose or mucin.
Figure 3B:
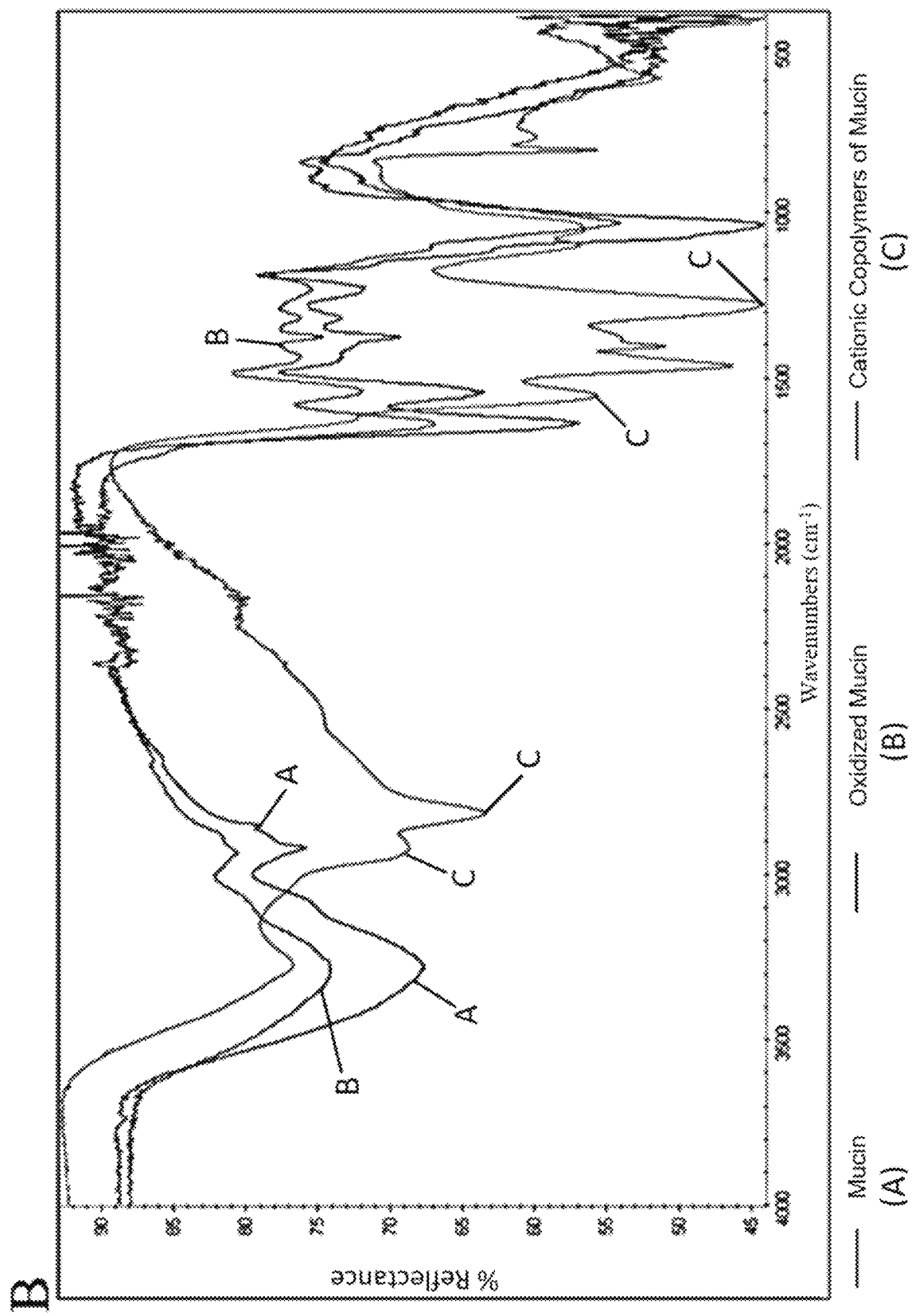

Fourier transform infrared spectroscopy (FTIR) is a technique which is used to obtain a spectrum of absorption or emission of a solid, liquid or gas. FIGS. 3A and 3B depict a Fourier transform infrared spectroscopy (FTIR) characterization of the polymers of cationic cellulose and cationic mucin III, respectively. In particular, FIG. 3A depicts the FTIR absorption spectra of cellulose, oxidized (2,3-dialdehyde) cellulose and the cationic copolymer of cellulose obtained by reacting 2,3-dialdehyde cellulose with polyethyleneimine (PEI) having a molecular weight of about 25,000. FIG. 3B depicts the FTIR absorption spectra of mucin III, oxidized mucin III and the cationic copolymer of mucin III obtained by reacting the oxidized mucin derivitised with polyethyleneimine having a molecular weight of about 25,000. As can be seen in FIGS. 3A and 3B, the cationic copolymers of cellulose and mucin, respectively, have significantly different absorption as compared to the native cellulose and mucin.

The chemical structure of cellulose, 2, 3-dialdehyde cellulose and copolymer of cellulose were identified with Fourier transform infrared spectroscopy (FTIR) and the results are shown in FIG. 3A. Characteristic peaks at 2940-2830 cm−1 (—C—H stretching), 1576 cm−1 (—N—H bending), and 1350-1000 cm−1 (—C—N stretching) can be found in the spectrum of novel copolymer of cellulose. Unlike PEI, the FTIR spectrum of novel cationic polymer displays a distinct peak at 1656 cm−1, which is the stretching band of —C=N, indicating the Schiff reaction between the amine groups of PEI and the aldehyde groups of 2, 3-dialdehyde cellulose.

The chemical structure of mucin, oxidized mucin and copolymer of mucin were identified with Fourier transform infrared spectroscopy (FTIR) and the results are shown in FIG. 3B. Characteristic peaks at 2940-2830 cm−1 (—C—H stretching), 1576 cm−1 (—N—H bending), and 1350-1000 cm−1 (—C—N stretching) can be found in the spectrum of copolymer of mucin.

The size of the microcarriers as well as the pore size of the microcarriers may be controlled by the reaction conditions, for example by the ratio of the substrate backbone component to the cationic site forming polymer depends upon the molecular weight of the polyamine. For example, polyethyleneimine (PEI) or poly(allylamine) (PLA) with molecular weight from about 15,000 Da to about 25,000 Da, the ratio of the oxidized cellulose to polyamine may range from about 50:1 to about 1:8. In one approach, when PEI and PLA with molecular weight ranging from about 65,000 to about 750,000 is used, the ratio of the oxidized cellulose to polyamine ranges from about 10:1 to about 1:20. In one form, to produce the microcarrier with uniform size, the copolymers were made more uniform by screening the wet material through a suitable mesh (16-150 mesh), such as having a median particle size from about 100 μm to about 1 mm in size.

As mentioned above, polysaccharide-polyamine copolymers and glycoprotein-polyamine copolymers resulting from the above-discussed reaction may have the following general formula:

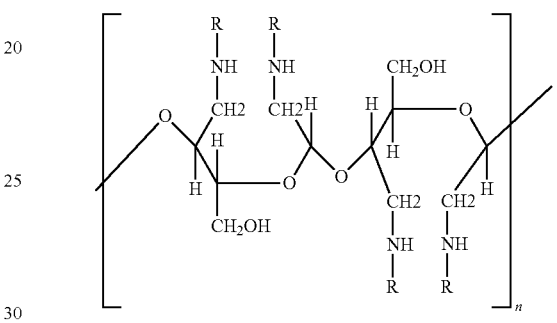

The polysaccharide-polyamine copolymers and glycoprotein-polyamine copolymers may be used in various ways to facilitate cell culture-based cell growth. For example, cell growth scaffolds may be made by way of coating the surfaces of existing cell culture scaffolds with the cationic copolymeric materials described herein to generate new scaffolds. In some approaches, the cationic copolymeric materials as described herein may be applied as coating materials, providing the neutral or negatively charged surfaces of polymers, glass, metals, and paper with a high density of cationic sites that advantageously facilitate attachment and growth of various mammalian cells.

In other approaches, existing cell growth scaffolds containing polysaccharides and glycoproteins may be converted into cationic scaffolds through transforming the polysaccharides or glycoproteins into cationic copolymers. For example, by transforming contained polysaccharides into cationic copolymers, cellulosic scaffolds can be converted into cationic scaffolds or grow matrices which allow the 3-D growth of mammalian cells and can be used as scaffolds for generation of artificial tissues.

FIGS. 5A and 5B illustrate comparisons of the proliferation and exogenous protein expression of cells HEK-293 which grow on surfaces coated with various materials, in this approach, poly 1-lysine (positive control), cationic copolymers of cellulose, and cationic copolymers of mucin. In particular, FIG. 5A illustrates the effect of the selected coating material on the proliferation of cells. As can be seen in FIG. 5A, the cells proliferate slower when they grow on surfaces coated with the cationic copolymers of cellulose and the cationic copolymers of mucin polymers as compared with the surface coated with poly 1-lysine. FIG. 5B illustrates the effect of the selected coating material on the level of exogenous protein expression. As can be seen in FIG. 5B, the cells express higher level of exogenous proteins when they grow on the surfaces coated with the cationic copolymers of cellulose and the cationic copolymers of mucin compared to the surface coated with poly 1-lysine. As such, the surfaces coated with cationic copolymers advantageously support longer periods of cell growth while expressing higher levels of exogenous protein production compared to the surface of substrates coated with poly 1-lysine.

Figures 7A, 7B, 7C:
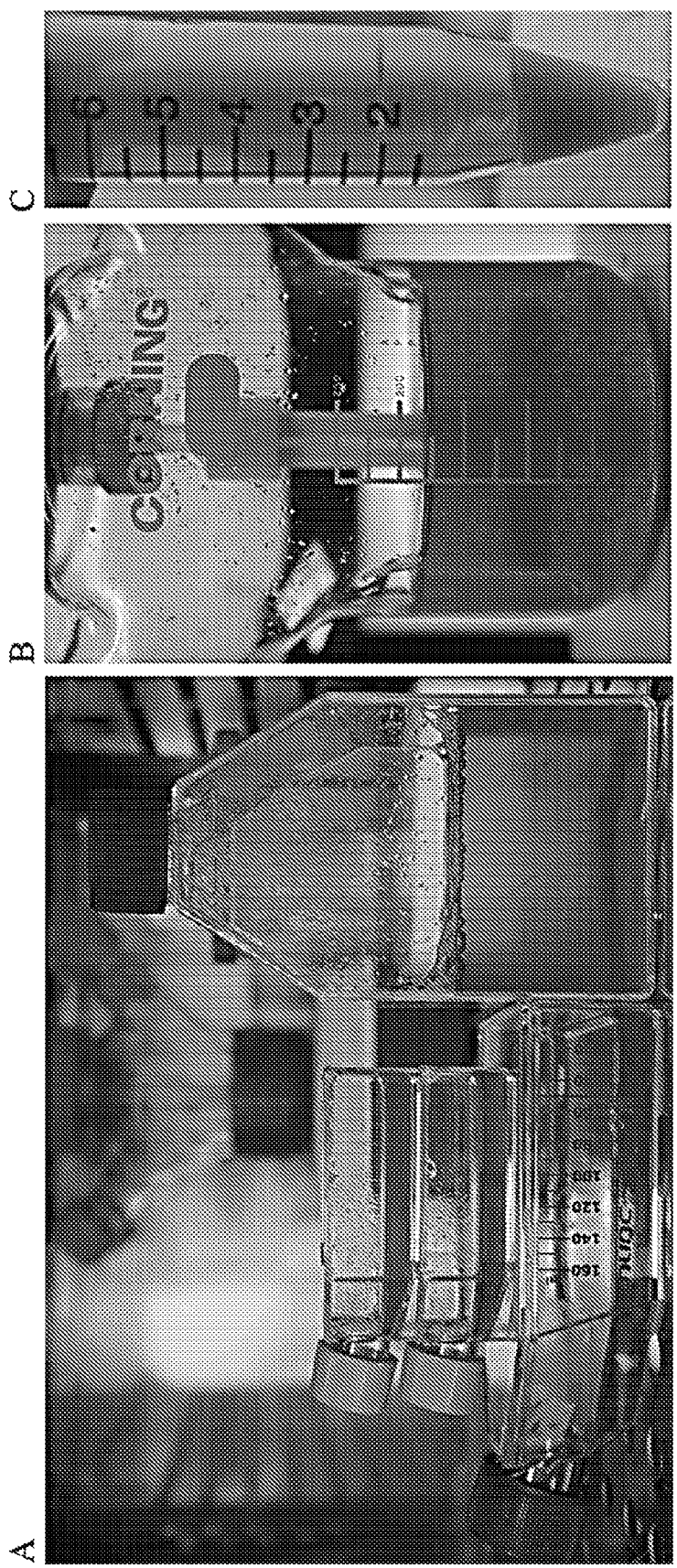
FIGS. 7A-7C show exemplary methods of culturing human cells utilizing microcarriers described herein, with FIG. 7A showing cell culturing in culture flasks without agitation, FIG. 7B showing cell culturing in a spin flask, and FIG. 7C showing cell culturing in a tube without agitation.

The microcarriers as described herein may be used to grow cells, for example, suspended in a medium including the microcarriers and in a culture flask without agitation, as shown in FIG. 7A, in a spin flask as shown in FIG. 7B, in a tube without agitation, as shown in FIG. 7C. As such, the microcarriers can significantly simplify the procedures and condition of culturing the mammalian cells. By one approach, for example, the microcarriers made of polyethyleneimine cellulosic copolymers, may be suspended in a cell growing medium at about 1% to about 50% by weight of the cell growing medium.

The microcarriers described herein may advantageously provide for mammalian cell growth in a 3-D suspension pattern. This is shown for example, in FIGS. 8A-8P, illustrating inverted fluorescence phase contrast microscope images of cultures of HEK-293 cells overexpressing green fluorescent protein (GFP) using various microcarriers made of various cationic polymers. In one approach, HEK-293 cells were cultured with low level oxidized cellulose, having about 50% of the glucose units oxidized, polymerized with polyethyleneimine with molecular weight of about 25,000 or 750,000, and microscope images were obtained on day 1 (FIG. 8A), day 3, (FIG. 8B), day 6 (FIG. 8C), and day 9 (FIG. 8D).

In another approach, HEK-293 cells were cultured with high level oxidized cellulose, having about 80% of the glucose units oxidized, polymerized with polyethyleneimine with molecular weight of about 25,000, and 3-D microscope images were obtained on day 1 (FIG. 8E), day 3, (FIG. 8F), day 6 (FIG. 8G), and day 9 (FIG. 8H). In yet another approach, HEK-293 cells were cultured with highly oxidized cellulose, having about 80% of the glucose units oxidized, polymerized with polyethyleneimine with molecular weight of about 750,000, and 3-D microscope images were obtained on day 1 (FIG. 8I), day 3, (FIG. 8J), day 6 (FIG. 8K), and day 9 (FIG. 8L). In still another approach, HEK-293 cells were cultured with highly oxidized mucin, having about 90% of the glucose units oxidized, polymerized with polyethyleneimine with molecular weight of about 25,000, and 3-D microscope images were obtained on day 1 (FIG. 8M), day 3, (FIG. 8N), day 6 (FIG. 8O), and day 9 (FIG. 8P). As can be seen most clearly in FIGS. 8D, 8H, 8K, and 8P, the amino cellulosic copolymer (FIGS. 8D, 8H, and 8K) and the amino cellulosic copolymer advantageously provide for mammalian cell growth in 3-D suspension pattern.

While FIGS. 8A-8P indicate that the cationic microcarriers may support HEK-293 cell growth in a 3-D suspension pattern for up to 9 days, it will be appreciated that the cationic microcarriers support HEK-293 cell growth in a 3-D suspension pattern for periods of time significantly longer than 9 days. For example, FIGS. 9A-9D show that the cationic microcarriers support long term growth (e.g., between 9 days and 35 days) of mammalian cells such as HEK-293 in a 3-D suspension pattern. It will be appreciated that depending on the microcarriers used, mammalian cells may be grown in a 3-D suspension pattern provided by the microcarriers for periods of time longer than 35 days, for example for about 35 to about 45 days, and longer than 45 days. The HEK-293 cells are shown in the drawings by way of example only, and other mammalian cells may be successfully grown using the microcarriers as described herein. In one exemplary approach, xenograft tumor growth may be supported by applying the porous microcarriers to a suitable surface.

FIGS. 6A-6H show transformations of starting materials such as a Texwipe (FIG. 6A), a cotton filter pad (FIG. 6B), mucin III (FIG. 6C), and microcrystalline cellulose (FIG. 6D) into scaffolds made of cationic Texwipe (FIG. 6E), scaffolds made of cationic cotton filter pad (FIG. 6F), microcarriers made of cationic mucin (FIG. 6G), and microcarriers made of cationic cellulose (FIG. 6H) using the above described methods. In one approach, paper and cloth-based scaffolds may be made by running the reactions on the scaffold material, thereby directly transforming the scaffold material itself. In one approach, the cationic polymer material as described herein may be premade and then a scaffold such as glass or plastic-based scaffold may be dipped into the cationic polymer material.

It will be appreciated that FIGS. 6A-6H show only a few possible microcarriers, matrices and scaffolds and other microcarriers, matrices and scaffolds usable to advantageously provide high density cell growth according to the principles described herein. Such cationic polymer-based scaffolds advantageously enhance the growth of mammalian cells, as shown for example in FIGS. 11B, 11C, 11E, and 11F, showing 3-D microscope images of cells overexpressing green fluorescent protein advantageously spreading and growing in cellulosic cationic scaffolds instead of forming single colonies in untreated cellulosic paper (FIG. 11A) and filter pad (FIG. 11D).

EXAMPLES

Example 1

Soluble 2,3-dialdehyde cellulose (DAC) or selectively oxidized mucin (SOM) may be prepared by sodium periodate oxidation of cellulose. 10 g of cellulose (size: <100 nm, 20 µm, 50 µm or fiber) or 5 g of mucin (Type II or III) may be resuspended with 200 mL deionized water. Next, 20 g sodium periodate is added and then the pH adjusted to 3.0 with 6×HCl. Next, the composition is degassed and purged with nitrogen gas and then allowed to react at 60° C. with stirring for 4 hours in dark at pH 3. The reaction is stopped by adding 10 mL of ethylene glycol. Dialysis the product against deionized water for 3 days. The soluble DAC or SOM is collected as supernatant by centrifugation at 40,000×g for 30 minutes to remove insoluble DAC or SOM as pallets. The collected supernatant may then be freeze dried (optional).

Example 2

In another example, (low oxidized) insoluble 2,3-dialdehyde cellulose (DAC) or selectively oxidized mucin (SOM) may be prepared by sodium periodate oxidation of cellulose. 10 g of cellulose (size: <100 nm, 20 µm, 50 µm or fiber) or 5 g of mucin (Type II or III) is resuspended with 200 mL deionized water and then 10 g sodium periodate is added. The pH is then adjusted to 3.0 with 6×HCl followed by degassing and purging with nitrogen gas. The composition is then reacted at 60° C. with stirring for 4 hours in dark at pH 3. The reaction can be stopped by adding 10 mL of ethylene glycol. The product was washed with 4 liters of deionized water 3 times, 1 hour for each time. The insoluble DAC or SOM is collected by centrifugation at 800×g for 10 minutes. The washed insoluble DAC or SOM solution can then be resuspended with DI water. The washed insoluble DAC solution can then by freeze dried (optional).

Example 3

Polysaccharide-polyamine copolymers and glycoprotein-polyamine copolymers can be synthesized by reacting DAC or SOM with branched polyethyleneimine (PEI) (MW 750K). The ratio of DAC/SOM to PEI is from 50:1 to 1:10. The branched polyethyleneimine, 10 g, (MW 750K, 50 wt. % in $H_2O$) was added into a 500 mL beaker. The pH of PEI was adjusted to 5.0 with 37% HCl. The pH of 100 ml of DAC solution or SOM solution, containing proper amount of DAC or SOM, was adjusted to 5.0 by adding 6×HCl. The solutions of PEI and solution of DAC or SOM were incubated on ice for 10 minutes. The solution containing 10 g of PEI and solution containing proper amount of DAC or SOM were mixed and incubated on ice at 1000 RPM for 5 minutes. The mixture was kept on ice without agitation until product was completely formed. The mixture was incubated at 70° C. for 60 minutes. The pH of the suspension was checked every 10 minutes and adjusted to 8.5 with 5M sodium hydroxide solution. The product was forced to pass mesh screen to achieve particles with a uniform size of diameter. The particles were incubated with 4 liters of 50 mM $Na_2CO_3$ solution for 30 minutes with stirring and precipitated by gravity. After the supernatant was aspirated, the precipitated particles were washed with 4 liters deionized water for one time for 10 minutes and precipitation by gravity. After removing the supernatant, the precipitated particles were suspended and incubated in 4 liters sodium acetate solution at pH 5.5 or 4 liters of 100 mM sodium bicarbonate solution at pH 8.5 with stirring for 72 hours at room temperature. Then the particles were collected by precipitation. After the supernatant was aspirated, the precipitated particles were washed with 4 liters deionized water for one time for 60 minutes and precipitated by gravity. The precipitated particles were resuspended with 500 mL deionized water and were reduced by adding 10 g sodium borohydride and incubated at room temperature for 72 hours. The reduced particles were washed with deionized water to remove the excessive sodium borohydride and PEI until pH of solution was between 5 and 6. The particles were kept in 25% ethanol alcohol at room temperature. The washed particles can then be freeze dried (optional).

Example 4

Polysaccharide-polyamine copolymers and glycoprotein-polyamine copolymers can be synthesized by reacting DAC or SOM with branched polyethyleneimine (PEI) (MW 25K). The ratio of DAC/SOM to PEI is from 50:1 to 1:5 w/w. The branched polyethyleneimine, 10 g, (MW 25K) was added into a 500 mL beaker. The pH of PEI was adjusted to 5.0 with 37% HCl. The pH of 100 ml of DAC solution or SOM solution, containing proper amount of DAC or SOM, was adjusted to 5.0 by adding 6×HCl. The solutions of PEI and solution of DAC or SOM were incubated on ice for 10 minutes. The solution containing 10 g of PEI and solution containing proper amount of DAC or SOM were mixed and incubated on ice at 1000 RPM for 5 minutes. The mixture was kept on ice without agitation until the product was completely formed. The mixture was incubated at 70° C. for 60 minutes. The pH of the suspension was checked every 10 minutes and adjusted to 8.5 with 5M sodium hydroxide solution. The product was forced to pass through a mesh screen to achieve particles with a uniform diameter. The particles were incubated with 4 liters of 50 mM $Na_2CO_3$ solution for 30 minutes with stirring and precipitated by gravity. After the supernatant was aspirated, the precipitated particles were washed with 4 liters of deionized water for 10 minutes and precipitated by gravity. After removing the supernatant, the precipitated particles were suspended and incubated in 4 liters of sodium acetate solution at pH 5.5 or 4 liters of 100 mM sodium bicarbonate solution at pH 8.5 with stirring for 72 hours at room temperature. Then the particles were collected by precipitation. After the supernatant was aspirated, the precipitated particles were washed with 4 liters of deionized water, for one time for 60 minutes, and precipitated by gravity. The precipitated particles were resuspended with 500 mL deionized water and were reduced by adding 10 g sodium borohydride and incubated at room temperature for 72 hours. The reduced particles were washed with deionized water to remove the excessive sodium borohydride and PEI until the pH of solution was between 5 and 6. The particles were kept in 25% ethanol alcohol at room temperature. The washed particles can then be freeze dried (optional).

Example 5

Polysaccharide-polyamine copolymers and glycoprotein-polyamine copolymers can be synthesized by reacting DAC or SOM with branched polyethyleneimine (PEI) (MW 750K). The ratio of DAC/SOM to PEI is from 50:1 to 1:10 w/w (titration method). The branched polyethyleneimine, 10 g, (MW 750K, 50 wt. % in $H_2O$) was added into a 500 mL beaker. The pH of PEI was adjusted to 5.0 with 37% HCl. The total volume of PEI was increased to 50 ml by adding deionized water. The pH of 50 ml of DAC solution or SOM solution, containing proper amount of DAC or SOM, was adjusted to 5.0 by adding 6×HCl. DAC solution or SOM solution was slowly added into PEI solution at flow rate 5 ml/min with stirring at 800 RPM. The mixture was kept at room temperature with agitation for 1 hour. The pH of the suspension was checked every 10 minutes and adjusted to 8.5 with 5M sodium hydroxide solution. The mixture was incubated at 70° C. for 60 minutes. The pH of the suspension was checked every 10 minutes and adjusted to 8.5 with 5M sodium hydroxide solution. The product was forced to pass through a mesh screen to achieve particles with a uniform diameter. The particles were incubated with 4 liters of 50 mM $Na_2CO_3$ solution for 30 minutes with stirring and precipitated by gravity. After the supernatant was aspirated, the precipitated particles were washed with 4 liters of deionized water for 10 minutes and precipitated by gravity. After removing the supernatant, the precipitated particles were suspended and incubated in 4 liters of sodium acetate solution at pH 5.5 or 4 liters of 100 mM sodium bicarbonate solution at pH 8.5 with stirring for 72 hours at room temperature. Then the particles were collected by precipitation. After the supernatant was aspirated, the precipitated particles were washed with 4 liters of deionized water for 60 minutes and precipitated by gravity. The precipitated particles were resuspended with 500 mL deionized water and reduced by adding 10 g sodium borohydride and incubated at room temperature for 72 hours. The reduced particles were washed with deionized water to remove the excessive sodium borohydride and PEI until the pH of solution was between 5 and 6. The particles were kept in 25% ethanol alcohol at room temperature. The washed particles can be freeze dried (optional).

Example 6

Polysaccharide-polyamine copolymers and glycoprotein-polyamine copolymers can be synthesized by reacting DAC or SOM with branched polyethyleneimine (PEI) (MW 25K). The ratio of DAC/SOM to PEI is from 50:1 to 1:5 w/w (titration method). The branched polyethyleneimine, 10 g, (MW 25K) was added into a 500 mL beaker. The pH of PEI was adjusted to 5.0 with 37% HCl. The total volume of PEI was increased to 50 ml by adding deionized water. The pH of 50 ml of DAC solution or SOM solution, containing proper amount of DAC or SOM, was adjusted to 5.0 by adding 6×HCl. DAC solution or SOM solution was slowly added into PEI solution at flow rate 5 ml/min with stirring at 800 RPM. The mixture was kept at room temperature with agitation for 1 hour. The pH of the suspension was checked every 10 minutes and adjusted to 8.5 with 5M sodium hydroxide solution. The mixture was incubated at 70° C. for 60 minutes. The pH of the suspension was checked every 10 minutes and adjusted to 8.5 with 5M sodium hydroxide solution. The product was forced to pass through a mesh screen to achieve particles with a uniform diameter. The particles were incubated with 4 liters of 50 mM $Na_2CO_3$ solution for 30 minutes with stirring and precipitated by gravity. After the supernatant was aspirated, the precipitated particles were washed with 4 liters of deionized water for 10 minutes and precipitated by gravity. After removing the supernatant, the precipitated particles were suspended and incubated in 4 liters of sodium acetate solution at pH 5.5 or 4 liters of 100 mM sodium bicarbonate solution at pH 8.5 with stirring for 72 hours at room temperature. Then the particles were collected by precipitation. After the supernatant was aspirated, the precipitated particles were washed with 4 liters of deionized water for 60 minutes and precipitated by gravity. The precipitated particles were resuspended with 500 mL deionized water and reduced by adding 10 g sodium borohydride and incubated at room temperature for 72 hours. The reduced particles were washed with deionized water to remove the excessive sodium borohydride and PEI until the pH of solution was between 5 and 6. The particles were kept in 25% ethanol alcohol at room temperature. The washed particles can be freeze dried (optional).

Example 7

Cell microcarriers were incubated with 75% ethanol for 60 minutes and then washed three times with 1×PBS buffer at pH 7.0 and one time with culturing medium RPMI 1640. The microcarriers were then incubated overnight at least 12 hours with complete growth medium RPMI 1640 at 37° C. in 5% $CO_2$. Human embryo kidney cell (HEK-293) overexpressing GFP (green fluorescent protein) and EPO (erythropoietin) were treated with 0.5% trypsin EDTA at 37° C. for 5 minutes followed by neutralization with the complete growth medium. Cell clusters were then disassociated through pipetting and collected through centrifugation.

Cells were then mixed with cell carriers and incubated for 4 hours at 37° C. in 5% $CO_2$ followed by adding 10 times of bed volume of complete growth medium and culturing statically for an additional 48 hours. Cell carriers with attached cells were transferred into a cell culture spinner flask. Cells were cultured in suspension pattern at a low stirring speed (20-100 rpm). The culture medium was changed, when necessary, by precipitating the cells by gravity and changing the supernatant medium.

The cells were collected and lysed with same volume of lysis buffer (50 mM Tris, 0.8% Triton, 0.2% SDS, pH 7.4) and the fluorescent intensity of the total cells lysates was analyzed by spectrofluorometry. As shown in FIG. 10A, more green fluorescent protein was produced by growing the cells overexpressing the green fluorescent proteins in a culturing container such as a T25 (growth area=25 $cm^2$) cell culture polystyrene flask utilizing the cationic copolymer microcarriers, illustrating a significantly higher expression of green fluorescent protein in the cells grown in the T25 flask utilizing cationic cellulose polymers (CC) and cationic mucin copolymers (CM) as compared to the cells grown on the bottom surface of the conventional T25 flask (T25). FIG. 10B shows Western Blot Assay results of samples containing 30 µg of total proteins, indicating that more erythropoietin (EPO) was produced the by HEK-293 cells cultured with the cationic polymer microcarriers as compared to cells cultured in the conventional T75 flask by the conventional 2-D methods.

The cationic copolymer microcarriers, matrices and scaffolds as described herein advantageously provide a multiple-layer, porous, spongy structure that permits anchorage-dependent cells to grow in a three-dimensional pattern rather than in a monolayer active surface provided by conventional carriers. As such, the cationic copolymer microcarriers, matrices and scaffolds significantly increase cell density per unit volume of the culture medium or cell growth surface. In addition, the 3-D open architecture provided by the microcarriers, matrices and scaffolds as described herein minimizes the disturbances of cell growth caused by agitation of the culturing medium and provides a relatively stable microenvironment for cell proliferation. The surfaces of the present cationic copolymer microcarriers, matrices and scaffolds contain positively charged sites and facilitates attachment and growth of cells thereon without the need for application of an external growth or attachment agent unlike the conventional microcarriers.

The microcarriers, matrices and scaffolds including the covalently cross-linked cationic copolymers as described herein may be used in various applications other than cell culturing. For example, the particles of the cationic copolymer may be suspended in a solution and this solution may be applied to tissue of an open wound to facilitate healing of the open wound. Instead of applying such a solution directly to a wound, the solution including the cationic copolymer particles as described herein may be applied to a material such as a wound dressing, which may then be applied to the wound of a human subject to facilitate the healing of the wound. Similarly, a solution including suspended cationic microcarrier particles as described herein may be applied to bone tissue to facilitate bone growth, to skin tissue to facilitate skin grafting.

Compared with the commercially available macrocarriers, the polysaccharide-polyamine copolymer carriers described herein show unique properties and advantages over other carriers. For example, the polysaccharide-polyamine carriers may be produced through a simple environmentally friendly polymerization reaction instead of a complex cross-linking reactions applied to produce materials such as Cytopore. Unlike the Cytoline containing two major components, the polysaccharide-polyamine copolymers only consist of a single synthetic compound, the copolymer. Therefore the production process is much simpler. Cultispher G and Cultispher S are made of cross-linked gelatin, which derived from collagen obtained from various animal by-products. The uncharged surface and relative higher production cost of gelatin are two drawbacks of Cultispher G and Cultispher S compared with the polysaccharide-polyamine copolymer carrier described herein.

The foregoing descriptions are not intended to represent the only forms of the cationic copolymers usable as novel cell growth microcarriers, scaffolds, and coatings. Similarly, while methods have been described herein in conjunction with specific embodiments, many alternatives, modifications, and variations will be apparent to those skilled in the art in light of the foregoing description.

What is claimed is:

1. Polysaccharide-polyamine copolymer or glycoprotein-polyamine copolymers having an amino functionality which will provide a cationic copolymeric material having a three-dimensional structure with cationic sites when protonated, the polysaccharide-polyamine copolymer comprising:
    a selectively oxidized polysaccharide or selectively oxidized glycoproteins, both the selectively oxidized polysaccharide and the selectively oxidized glycoproteins having a 2,3-dialdehyde moiety; and
    amino polymers which provide an amino functionality, the amino polymers cross-linking the oxidized polysaccharides to provide a particulate polysaccharide-polyamine copolymer or glycoprotein-polyamine copolymers having an amino functionality, the polysaccharide-polyamine copolymer or the glycoprotein-polyamine copolymers having a pore size configured to support cells on an interior surface,
    wherein the amino polymers have a nitrogen content of at least 0.5% and no more than 30 wt. %, based on the weight of the amino polymers, and wherein the amino polymers have a molecular weight in the range of from about 15,000 to about 900,000.

2. A method of producing the polysaccharide-polyamine copolymers or glycoprotein-polyamine copolymers according to claim 1, the method comprising the steps of:
    providing an oxidized polysaccharide or oxidized glycoprotein having aldehyde moieties;
    reacting the oxidized polysaccharide or oxidized glycoprotein with an amino polymer to form a polymer containing imine derivatives; and
    converting the imine derivatives on the polymer to amines to form the polysaccharide-polyamine copolymers or glycoprotein-polyamine copolymers, the polysaccharide-polyamine copolymers or glycoprotein-polyamine copolymers having an amino functionality which will provide a cationic copolymeric material having a three-dimensional structure with cationic sites when protonated.

3. The method of claim 2 wherein the polysaccharide-polyamine copolymers or glycoprotein-polyamine copolymers are di-block copolymers.

4. The method of any one of claim 2 wherein the aldehyde moieties are generated by selectively oxidizing hydroxyl groups on C2 and C3 of glucose units and the oxidation does not produce more carboxyl groups than aldehyde groups or cause cleavage of a polysaccharide chain.

5. The method of claim 2 further comprising the step of drying the polysaccharide-polyamine copolymers or glycoprotein-polyamine copolymers to form polysaccharide-polyamine copolymer particles or glycoprotein-polyamine copolymer particles.

6. The method of claim 2 wherein the selectively oxidized polysaccharide is selected from the group consisting of selectively oxidized cellulose, selectively oxidized starch, selectively oxidized amylose, selectively oxidized chitosan, selectively oxidized dextran, selectively oxidized glycogen, selectively oxidized chitin, polysaccharide side chain of mucin, and mixtures thereof, the polysaccharide having been oxidized in an amount effective to provide a 2,3-dialdehyde moiety which is reactive with the amino polymers.

7. The method of claim 2 wherein the amino polymers are selected from the group consisting of polyethyleneimine, poly(allylamine) and polypropylenimine tetramine, protein, polypeptides, and mixtures thereof.

8. The method of claim 2 wherein the polysaccharide-polyamine copolymer or cationic copolymer has particulates having an average pore sizes of greater than about 50 μm.

9. The polysaccharide-polyamine copolymer or the glycoprotein-polyamine copolymers of claim 1, wherein the selectively oxidized polysaccharide is selected from the group consisting of selectively oxidized cellulose, selectively oxidized starch, selectively oxidized amylose, selectively oxidized chitosan, selectively oxidized dextran, selectively oxidized glycogen, selectively oxidized chitin, polysaccharide side chain of mucin, and mixtures thereof, the polysaccharide having been oxidized in an amount effective to provide the 2,3-dialdehyde moiety which is reactive with the amino polymers.

10. The polysaccharide-polyamine copolymer or the glycoprotein-polyamine copolymers of claim 1, wherein the selectively oxidized polysaccharide have β-1,4-glycosidic bonds or β-1,6-glycosidic bonds.

11. The polysaccharide-polyamine copolymer or the glycoprotein-polyamine copolymers of claim 1, wherein the selectively oxidized polysaccharide have β-1,4-glycosidic bonds.

12. The polysaccharide-polyamine copolymer or the glycoprotein-polyamine copolymers of claim 1, wherein the selectively oxidized polysaccharide is selected from the group consisting of selectively oxidized cellulose, selectively oxidized chitosan, selectively oxidized chitin, selectively oxidized amylose and mixtures thereof.

13. The polysaccharide-polyamine copolymer or the glycoprotein-polyamine copolymers of claim 1, wherein the amino polymers which provide a cationic amino functionality are selected from the group consisting of polyethyleneimine, poly(allylamine) and polypropylenimine tetramine, protein, polypeptides, and mixtures thereof.

14. The polysaccharide-polyamine copolymer or the glycoprotein-polyamine copolymers of claim 1, wherein the amino polymers are in a linear, branched or dendritic form.

15. The polysaccharide-polyamine copolymers or the amino glycoprotein copolymers of claim 1, wherein the particulates of the polysaccharide-polyamine copolymer or the amino glycoprotein copolymers and cationic copolymeric material have sizes in the range of from about 100 μm to about 10 mm.

16. The polysaccharide-polyamine copolymer or the amino glycoprotein copolymers of claim 1, wherein the particulate polysaccharide-polyamine copolymer or cationic copolymeric material has particulates having an average pore sizes of greater than about 50 μm.

17. Polysaccharide-polyamine copolymer or glycoprotein-polyamine copolymers having an amino functionality which will provide a cationic copolymeric material having a three-dimensional structure with cationic sites when protonated, the polysaccharide-polyamine copolymer comprising:
    a selectively oxidized polysaccharide or selectively oxidized glycoproteins, both the selectively oxidized polysaccharide and the selectively oxidized glycoproteins having a 2,3-dialdehyde moiety; and
    amino polymers which provide an amino functionality, the amino polymers cross-linking the oxidized polysaccharides to provide a particulate polysaccharide-polyamine copolymer or glycoprotein-polyamine copolymers having an amino functionality, the polysaccharide-polyamine copolymer or the glycoprotein-polyamine copolymers having a pore size configured to support cells on an interior surface,
wherein the particulate polysaccharide-polyamine copolymer or cationic copolymeric material has particulates having an average pore sizes of greater than about 50 µm.

\* \* \* \* \*